(12) United States Patent
Demirli et al.

(10) Patent No.: US 8,290,257 B2
(45) Date of Patent: Oct. 16, 2012

(54) METHOD AND APPARATUS FOR SIMULATION OF FACIAL SKIN AGING AND DE-AGING

(75) Inventors: Ramazan Demirli, Whippany, NJ (US); Greg George Hillebrand, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1169 days.

(21) Appl. No.: 11/681,509

(22) Filed: Mar. 2, 2007

(65) Prior Publication Data
US 2008/0212894 A1    Sep. 4, 2008

(51) Int. Cl.
G06K 9/00    (2006.01)
(52) U.S. Cl. ......................................... 382/165; 382/128
(58) Field of Classification Search .................. None
See application file for complete search history.

(56) References Cited

U.S. PATENT DOCUMENTS

| | | | |
|---|---|---|---|
| 4,276,570 A * | 6/1981 | Burson et al. ................. | 382/276 |
| 6,283,858 B1 * | 9/2001 | Hayes et al. ..................... | 463/31 |
| 6,571,003 B1 | 5/2003 | Hillebrand et al. | |
| 6,734,858 B2 | 5/2004 | Attar et al. | |
| 6,761,697 B2 | 7/2004 | Rubinsten et al. | |
| 6,828,972 B2 * | 12/2004 | Zhang et al. ................... | 345/473 |
| 6,959,119 B2 | 10/2005 | Hawkins et al. | |
| 7,020,347 B2 | 3/2006 | Zhang et al. | |
| 7,200,281 B2 | 4/2007 | Zhang et al. | |
| 7,221,780 B1 * | 5/2007 | Wang ............................ | 382/118 |
| 2002/0054714 A1 | 5/2002 | Hawkins et al. | |
| 2003/0063794 A1 | 4/2003 | Rubinsten et al. | |
| 2004/0056857 A1 | 3/2004 | Zhang et al. | |
| 2005/0232506 A1 * | 10/2005 | Smith et al. ................... | 382/254 |
| 2006/0034542 A1 * | 2/2006 | Aoyama ......................... | 382/276 |
| 2006/0269111 A1 * | 11/2006 | Stoecker et al. .............. | 382/128 |
| 2006/0274071 A1 | 12/2006 | Bazin | |
| 2007/0189627 A1 * | 8/2007 | Cohen et al. .................. | 382/254 |

FOREIGN PATENT DOCUMENTS
JP    2002304619 A    10/2002
(Continued)

OTHER PUBLICATIONS

C. Choi, "Age Change for Predicting Future Faces," 1999 IEEE Intl. Fuzzy Systems Conf. Proceedings, Aug. 22-25, 1999, pp. 1603-1608.
(Continued)

*Primary Examiner* — Brian P Werner
*Assistant Examiner* — Tahmina Ansari
(74) *Attorney, Agent, or Firm* — S. Robert Chuey

(57) ABSTRACT

A novel method and system is disclosed to realistically simulate the progress or worsening of facial skin features that contribute to the overall look and condition of the skin. The method utilizes two close-up photographs of the face, one is captured with a digital camera in standard white light, and the other is captured with the same camera in UV light. Then, the method processes these images to simulate the progress or worsening of the major skin features: hyperpigmented spots, wrinkles and small texture features. The worsening of these features simulates facial skin aging due to prolonged exposures to sunlight, biological aging or degradation of the skin health. The progress of these features simulates the improvement of facial skin in terms of overall look and healthiness as though the patient has gone through a treatment. Therefore, the present invention discloses a series of methods that are useful in dermatology, cosmetics and computer animations.

6 Claims, 16 Drawing Sheets

FOREIGN PATENT DOCUMENTS

JP 2004326488 A 11/2004

OTHER PUBLICATIONS

A.J. Bailey, "Molecular mechanisms of ageing in connective tissues," Mechanisms of Ageing and Development 122 (2001) 735-755.
A. Bastanfard et al., "Toward E-appearance of Human Face and Hair by Age, Expression and Rejuvenation," Proceedings of the 2004 Intl. Conf. on Cyberworlds, IEEE.
L. Boissieux et al., "Simulation of Skin Aging and Wrinkles with Cosmetics Insight," MIRALab, Univ. of Geneva, 1999 or later.
O.G. Cula et al., "Skin Texture Modeling," Intl. Journal of Computer Vision 2004.
H.K. Hussein, "Towards Realistic Facial Modeling and Re-Rendering of Human Skin Aging Animation," Proc. of the Shape Modeling Intl. 2002, IEEE.
P.E. Hysert et al., "At Facce Value: age progression software provides personalised demonstration of the effects of smoking on appearance," Tob. Control 2003; 12;238.
M.S. Kaminer, "Photodamage: Magnitude of the Problem," Blackwell Science, Photodamage, 1994 or later.
A. Lanitis et al., "Toward Automatic Simulation of Aging Effects on Face Images," IEEE Trans. on Pattern Analysis and Machine Intel., vol. 24, No. 4, Apr. 2002.
C. Larboulette et al., "Real-Time Dynamic Wrinkles," Gravir & Siames-Irisa, France, Oct. 2002 or later.
W.-S. Lee et al., "Cloning and Aging in a VR Family," MIRALab, Univ. of Geneva, 1998 or later.
J.J. Leyden, "Clinical features of ageing skin," British Journal of Dermatology (1990) 122, Supplement 35, 1-3.
Z. Liu et al., "Expressive Expression Mapping with Ratio Images," ACM SOGGRAPH 2001, Aug. 12-17, 2001.
N. Magnenat-Thalmann et al., "A Computational Skin Model: Fold and Wrinkle Formation," IEEE Trans. on Info. Tech. in Biomedicine, vol. 6, No. 4, Dec. 2002.
R. Marks, "Sun-damaged Skin," Martin Dunitz Ltd. 1992, pp. 13-34.
J.P. Ortonne, "Pigmentary changes of the ageing skin," British Journal of Dermatology (1990) 122, Supplement 35, 21-28.
G.E. Pierard et al., "From skin microrelief to wrinkles. An area ripe for investigation," Journal of Cosmetic Dermatology, 2.21-28, 2004.
P. Quatresooz et al., "The riddle of genuine skin microrelief and wrinkles," Intl. Journal of Cosmetic Science, 2006, 28, 389-395.
Y. Wu et al., "Physically-based Wrinkle Simulation & Skin Rendering," MIRALab, University of Geneva, 1998.
Y. Wu et al., "Simulating wrinkles and skin aging," The Visual Computer (1999) 15:183-198.
Y. Wu et al., "A Dynamic Wrinkle Model in Facial Animation and Skin Aging," MIRALab, University of Geneva, 1998.
V. Wu et al., "Skin Aging Estimation by Facial Simulation," MIRALab, Univ. of Geneva, 1999 or later.
Y. Zhang et al., "Realistic and Efficient Wrinkle Simulation Using an Anatomy-based Face Model with Adaptive Refinement," Proc. of Computer Graphics Intl. 2005, Jun. 22-24.
Y. Sun et al., "A Novel Method of Recognizing Ageing Face Based on EHMM," Proc. of the Fourth Intl. Conf. on Mach. Learning and Cybernetics, IEEE, Aug. 18-21, 2005.
S. Alaluf et al., "The Impact of Epidermal Melanin on Objective Measurements of Human Skin Colour," Pigment Cell Res 15:119-126. 2002.
J. Canny, "A Computational Approach to Edge Detection," IEEE Trans. on Pattern Analysis and Mach. Intel., vol. 4, PAMI-8, No. 6, Nov. 1986.
W.T. Freeman et al., "The Design and Use of Steerable Filters," IEEE Trans. on Pattern Analysis and Mach. Intel., vol. 13, No. 9, Sep. 1991.
R.-L. Hsu et al. "Face Detection in Color Images," IEEE Trans. on Pattern Analysis and Mach. Intel., vol. 24, No. 5, May 2002.
N. Kollias et al., "Fluorescence photography in the evaluation of hyperpigmentation in photodamaged skin," Jrnl. of Amer. Acad. of Dermatology, vol. 36, No. 2, 1997.
N. Kollias et al., "Optical Non-Invasive Approached to Diagnosis of Skin Diseases," Soc. for Investigative Dermatology, vol. 7, No. 1, Dec. 2002.
M. Lievin et al., "Nonlinear color space and spatiotemporal MRF for hierarchical segmentation of face features in video," IEEE Trans. on Image Proc., vol. 13, No. 1, Jan. 2004.
K. Miyamoto et al., "Development of a digital imaging system for objective measurement of hyperpigmented spots on the face," Skin Research and Tech. 2002, 8:227-235.
N. Otsu, "A Threshold Selection Method from Gray-Level Histograms," IEEE Trans. on Systems, Man and Cybernetics, vol. SMC-9, No. 1, Jan. 1979.
Q. Hu et al., "Supervised Range-Constrained Thresholding," IEEE Trans. on Image Processing, vol. 15, No. 1, Jan. 2006.
B.S. Reddy et al., "An FFT-Based Technique for Translation, Rotation, and Scale-Invariant Image Registration," IEEE Trans. on Image Processing, vol. 5, No. 8, Aug. 1996.
J. Staal et al., "Ridge-Based Vessel Segmentation in Color Images of the Retina,"IEEE Trans. on Medical Imaging, vol. No. 4, Apr. 2004.
G.N. Stamatas et al., "Non-Invasive Measurements of Skin Pigmentation in Situ," Pigment Cell Res. 17: 618-626, 2004.
Canfield Imaging Systems, "VISIA Complexion Analysis," Brochure 0701-16.

* cited by examiner

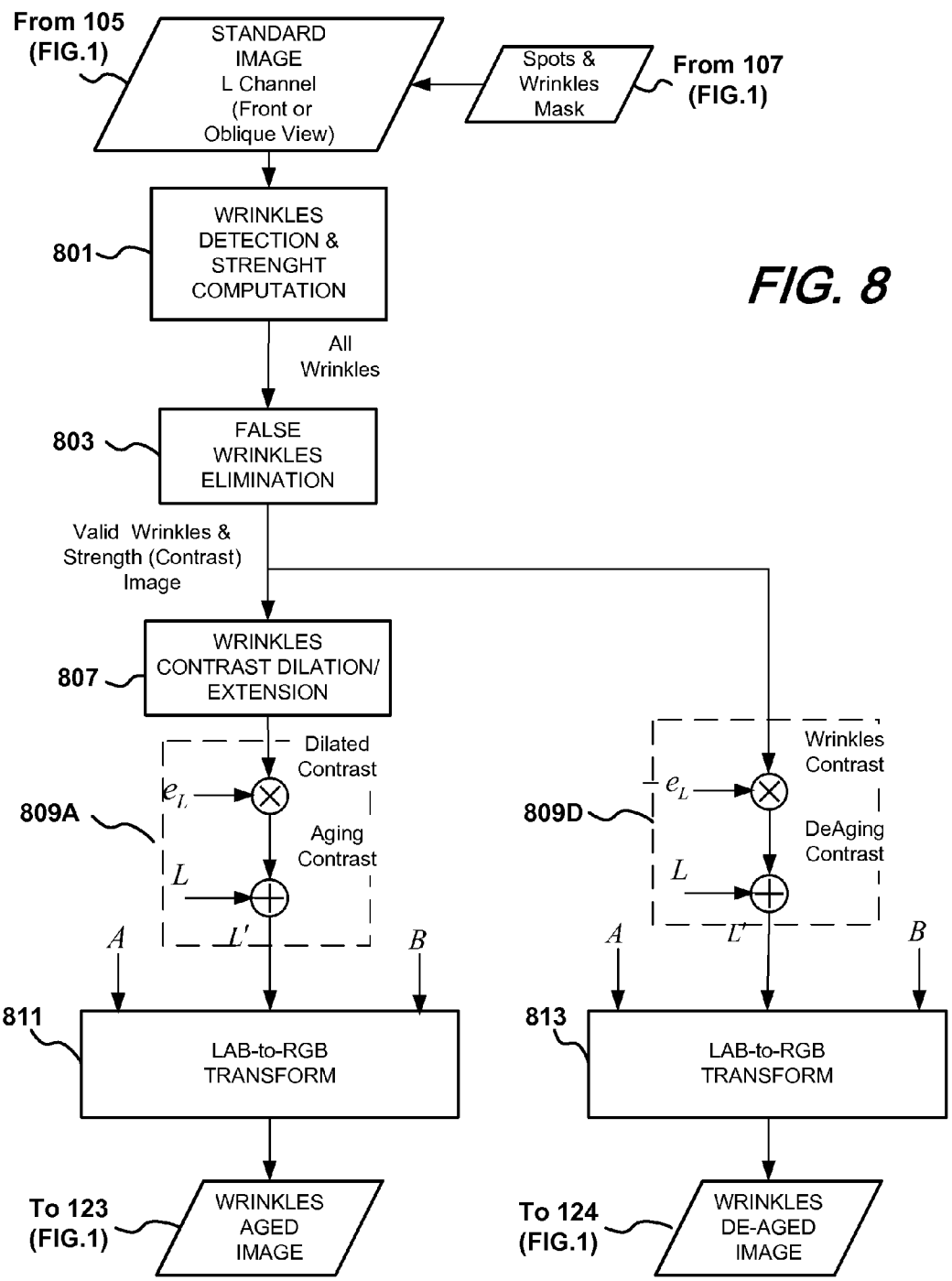

METHOD AND APPARATUS FOR SIMULATION OF FACIAL SKIN AGING AND DE-AGING

FIELD OF THE INVENTION

The present invention relates to the field of image processing and simulation, particularly to the generation of images depicting the simulated aging or de-aging of skin.

BACKGROUND INVENTION

The effects of skin aging on the appearance of the human face are well studied and documented in dermatology. Each individual's skin aging progression is dependent on both intrinsic and extrinsic factors. Intrinsic factors, such as gender, race, and skin pigmentation, are genetically programmed and unique for each individual and can affect the rate of dermal thinning, loss of mechanical elasticity, and other well-characterized histological and bio-mechanical changes with age. Intrinsic factors affect both sun-protected and sun-exposed body sites. Extrinsic factors include an individual's diet, lifestyle, skin care habits and sun exposure history. Chronic sun exposure is well-known to accelerate the onset time and severity of skin aging. All exposed body sites including the face have some degree of skin photoaging. (Gilchrest., B. *Photodamage*, Blackwell Science, Inc. 1995).

One of the most visually prominent features of photoaged skin is a mottled and irregular pigmentation that appears as a spot with dark brown coloration on the skin (Griffiths C. E. M., "The clinical identification and quantification of photodamage," *Brit. J. Derm.*, Vol. 127 (Suppl. 41), 37-42, 1992; K. Miyamoto et al., "Utilization of a high-resolution digital imaging system for the objective and quantitative assessment of hyperpigmented spots on the face," *Skin Research and Technology*, Vol. 8, No. 2 pp: 73-78, May 2002, hereinafter the "Miyamoto reference"). These hyperpigmented lesions are called age spots, liver spots, lentigo senilis, or actinic lentigines. Hyperpigmentation in photodamaged skin can be better visualized using methods that reveal subsurface pigmentation not visible with standard white light. One method, called UV-excited fluorescence photography, which was originally introduced by Kollias (Kollias et al., "Fluorescence photography in the evaluation of hyperpigmentation in photodamaged skin", *J Am Acad Dermatol.*, Vol. 36, pp: 226-230, 1997), involves imaging the skin under narrow-band UVA centered at 365 nm. Epidermal melanin absorbs strongly in this UVA range, approximately 3-5 times its absorption in the visible spectrum. Any UVA that is not absorbed by epidermal melanin enters the dermis where it is scattered and absorbed by collagen and elastin fibers which convert some of the absorbed energy to fluorescence. The wavelength of maximum collagen emission occurs in the visible spectrum, centered at 420 nm. The in vivo absorption of melanin at 420 nm is two times greater than at 540 nm. Thus, the total amount of UVA that enters the skin and reaches the dermis is attenuated by epidermal melanin approximately 5-fold and the amount of visible fluorescence is attenuated by the same epidermal melanin approximately 2-fold. In other words, epidermal melanin detection with UV-excited fluorescence is about 10 times more sensitive compared to visible light. This enhancement in sensitivity allows for the detection of hyperpigmented spots that cannot be seen under normal white light imaging methods. Hyperpigmentation spots that cannot be observed with visible light will, without intervention, become darker and more visibly apparent under normal visible light at a later point in life.

Other prominent features of aged skin are rough texture and skin wrinkles (Leyden J. J. "Clinical features of ageing skin", *Br. J. Dermatol*. Vol. 122, Suppl. 35, pp: 1-3, 1990) caused in part by the gradual alteration and loss of dermal connective tissues such as collagen, especially in sun-exposed areas of the body (Bailey, Molecular mechanisms of aging in connective tissues, *Mech. Aging Dev.*, Vol. 122, No. 7, pp.: 735-755, 2001). Hyperpigmentation, wrinkles and rough texture are visible skin features that play an important role in the overall appearance and healthiness of skin.

It is of practical value to be able to accurately simulate the aging process. Aging simulation has several useful applications such as computer animation, facial recognition, missing person identification, entertainment, medicine and cosmetics. Various models have been employed to enable the realistic simulation of an aging face including geometric-models, physically-based models, image-based models or bio-mechanical models (Hussein, K. H, Toward realistic facial modeling and re-rendering of human skin aging animation, *Proceedings of the Shape Modeling International* 2002, IEEE Computer Society, 2002). Attempts have been made to customize aging simulation so that it more accurately depicts a particular person's future aged appearance. For example, aging algorithms have been developed based on a population cohort of images combined with published data regarding facial changes associated with aging in order to simulate an aged appearance of an individual (Hysert P E et al. "*At Face Value*": age progression software provides personalized demonstration of the effects of smoking on appearance," Tobacco Control, Vol. 12, pp: 238-240, 2003). A limitation of this method is that the aged image is a reflection of population norms, and does not necessarily reflect the individual's unique aging process.

Boissiux et al. developed an image-based model for simulating skin aging whereby generic masks of pre-computed wrinkles are applied as textures on a 3D model of a person's face. Eight basic masks are employed and the particular mask used is matched to the person's gender, shape of face and type of expression being simulated (Boissiux et al. "Simulation of skin aging and wrinkle with cosmetic insight", *Computer Animation and Simulation*, pp 15-27, 2000). This approach, because it relies on population means, is limited in its ability to accurately predict each person's unique skin features that will appear with age.

Zhang et al. describes a method for transferring the geometric details of an old face onto that of a young face in order to make the young face look old (Zhang et al. "System and method for image-based surface detail transfer" US7020347B2, 2006). Conversely, the surface details of a young face can be transferred to that of an old to make an old face look young. This approach is limited by the fact that the aging features of the old face will not be exactly the same features that the young face will eventually realize.

SUMMARY OF THE INVENTION

The present invention is directed toward processing methods and apparatus which process facial images to detect and manipulate skin features such as hyperpigmented spots, wrinkles and fine texture features in order to overcome the aforementioned limitations. In one aspect of the present invention, computer-implementable methods are provided to detect and delineate the relevant portions of a digital facial image within which the aforementioned skin features are detected. Further computer-implementable methods are used to detect the skin features and to manipulate them such as by emphasizing or and de-emphasizing their appearance so as to simulate aging and/or de-aging of the skin.

In a further aspect of the present invention, digital images captured under UV illumination are processed to detect the presence of spots not visible under standard lighting conditions and to predict their growth and potential visibility.

Methods are presented for discriminating amongst various types of facial features (e.g., spots vs. wrinkles vs. textures vs. other features) and appropriately simulating the aging and de-aging of facial features based on their type.

The above and other aspects and features of the present invention will be apparent from the drawings and detailed description which follow.

BRIEF DESCRIPTION OF THE DRAWINGS

FIG. 8 is a flowchart of an exemplary wrinkle aging and de-aging simulation process in accordance with the present invention.

DETAILED DESCRIPTION

Overview of Exemplary Embodiment

Figure 1:
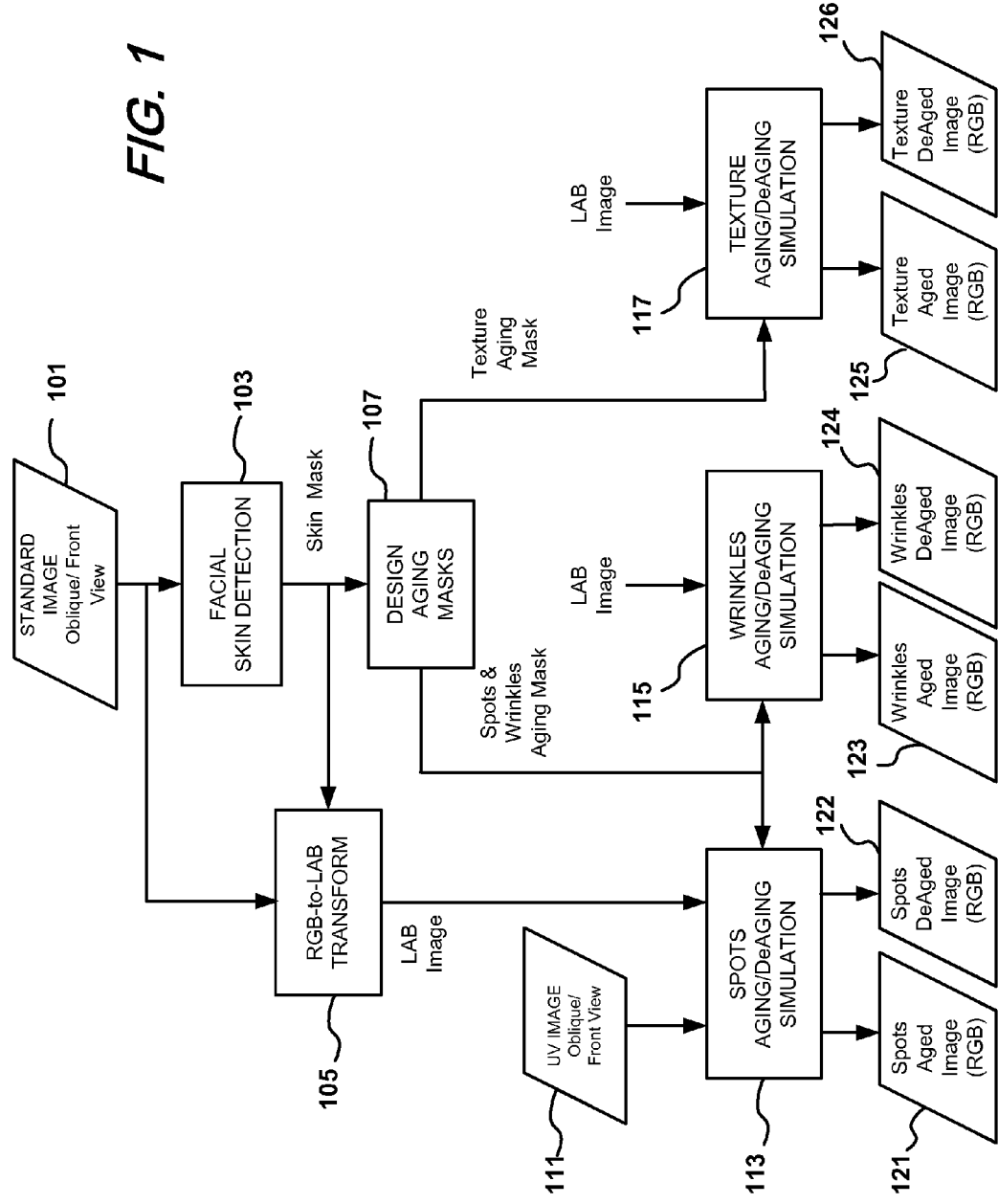
FIG. 1 is a high-level flowchart illustrating an exemplary aging/de-aging simulation method for spots, wrinkles and texture of facial skin, in accordance with the present invention.

FIG. 1 is a high-level flowchart illustrating an exemplary aging/de-aging simulation method for spots, wrinkles and texture of facial skin, in accordance with the present invention. At 101, a close-up facial photograph captured under standard light, such as with a conventional a digital camera, is provided as an input. At 111, a photograph of the same subject, captured under UV lighting modality (UV light source with a UV filter in front of the camera) is also provided as an input. In order to provide standardized and reproducible illumination conditions and image registration, the two images are preferably captured with an automated and controlled facial image capture system, such as the VISIA Complexion Analysis System (hereafter refereed to as VISIA) available from Canfield Scientific, Inc. Furthermore, the two pictures preferably should be captured from an oblique view to better display the cheek area with large skin patch.

As is typical, the standard light image input at 101 will be expressed as an RGB (red, green, blue) color image. Note, however, that the present invention is not limited to any particular format. At step 105, the RGB image is transformed into the 1976 CIE L*a*b* color space. Such a color transformation is commonly used in the art to separate the luminance and chrominance components of an image. The L*a*b* transformation hereafter will be called LAB transformation, and the transformed image will be referred to as an LAB image. The L channel of the LAB image represents the luminosity whereas the A and B components represent the chromaticity. Several skin feature analysis and re-synthesis operations described herein are performed on the LAB image. Although the various embodiments described show use of the LAB color space format, it is possible that other color space formats comprising luminance and chrominance components may be used to practice the present invention.

At 103, facial skin detection is performed, which entails the determination of those pixels from the full-face image which represent skin (as opposed to hair, eyes, lips, nasal labial folds, etc.) A facial skin detection process is described below.

Operation then proceeds to 107 in which, based on the skin pixels determined at 103, specific areas of the face, or "masks," are delineated for performance of the spots, wrinkles and texture aging simulations. A first mask is generated for spots and wrinkles simulation that covers certain parts of the face, and a second mask is generated for texture simulation, covering certain parts of the face. The mask generation process is described in detail below.

Aging and de-aging simulations of spots, wrinkles and texture are carried out at 113, 115, and 117, respectively. The Spots Aging/De-Aging Simulation at 113 receives the LAB transformed standard image (from 105) and the UV image in the RGB domain (from 111) along with the "spots and wrinkles aging mask" (from 107) and generates a spots aged image, at 121, and a spots de-aged image, at 122.

The Wrinkles Aging/De-Aging Simulation at 115 receives the LAB transformed image (from 105) along with the "spots and wrinkles aging mask" (from 107) and generates wrinkles aged and de-aged images at 123 and 124, respectively.

The Texture Aging/De-Aging Simulation at 117 receives the LAB transformed image (from 105) along with the texture aging mask (from 107) and generates texture aged and de-aged images at 125 and 126, respectively.

Implementations of the aging and de-aging simulation of spots (113), wrinkles (115), and texture (117) are described below in greater detail as well as the generation of compound images in which the individual aged and de-aged images are combined. An interactive slider application to demonstrate the transition between aged and de-aged images on a computer monitor is also described below.

Figure 11:
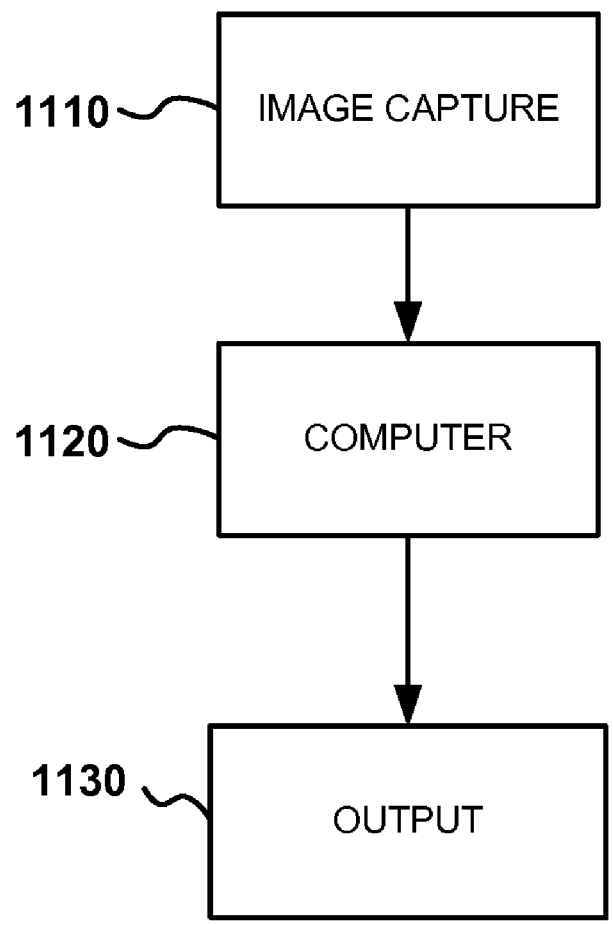
FIG. 11 is a block diagram of an exemplary embodiment of a system for carrying out the present invention.

FIG. 11 is a block diagram of an exemplary embodiment of a system 1100 that can be used to carry out the present invention. As shown in FIG. 11, the system 1100 comprises an image capturing sub-system 1110, such as the aforementioned VISIA Complexion Analysis System, or the like, coupled to a general purpose computer 1120, which is in turn coupled to an output device 1130. The computer 1120 may be a personal computer, or the like, programmed to operate in accordance with the present invention. The output device 1130 may include one or more of a variety of devices, such as: a conventional computer monitor, or the like, which the computer 1120 controls to display images, such as the results of the various simulations carried out in accordance with the present invention; a printing device; a storage device; and a communications device, among others. As can be appreciated, the present invention can be implemented with a wide variety of hardware configurations and is not limited to the system of FIG. 11.

Facial Skin Detection

Aging simulation based on skin features should be performed on the skin regions of the face. In the exemplary embodiment of the present invention, non-skin regions of face, such as lips, hair, eyes, eye brows, nostrils, etc. are excluded from the simulation. The skin regions of the face are determined from the standard face image. Several skin detection algorithms have been developed for a variety of purposes, including face detection. (See, e.g., R. L. Hsu et al., "Face detection in color images", *IEEE Transactions on Pattern Analysis and Machine Intelligence*, Vol. 24, No. 5, pp. 696-707, May 2002.) If such skin detection algorithms provide an adequate level of granularity, they may be used for facial skin aging simulation in accordance with the present invention.

As an alternative, the skin detection (and subsequent mask generation) can be performed manually, i.e., with user input. Given a facial image, a user can outline the skin regions of the face using conventional computer-based drawing techniques. The outlines would thus define the masks to be used by the aging/de-aging simulations. Although computationally simple, this approach has several drawbacks. It carries a risk of including non-skin parts of face in the simulation, and also introduces subjectivity inherent in human involvement, leading potentially to wide variations in results.

In a preferred embodiment, a novel skin detection algorithm is used which segments only the uniformly lighted portions of facial skin based on an oblique-view or front-view image and excludes the non-skin regions (eyes, eyebrows, hair, mustache, and beard) as well as shadowy skin regions (such as the neck area). The skin detection is performed based on the Individual Typology Angle (ITA) measure which is computed from the L, A, and B measurements. (See G. N. Stamatas et al., "Non-Invasive Measurements of Skin Pigmentation In Situ," *Pigment Cell Research*, Vol. 17, pp: 618-626, 2004.) The ITA is defined for each image pixel (i,j) as arc tan $((L[i,j]-50)/B[i,j])$ and related to the melanin concentration in skin. The hypothesis is that the ITA values for skin pixels will be clustered around a value whereas the ITA values for non-skin pixels are markedly away from the ITA value of skin pixels.

Figure 2:
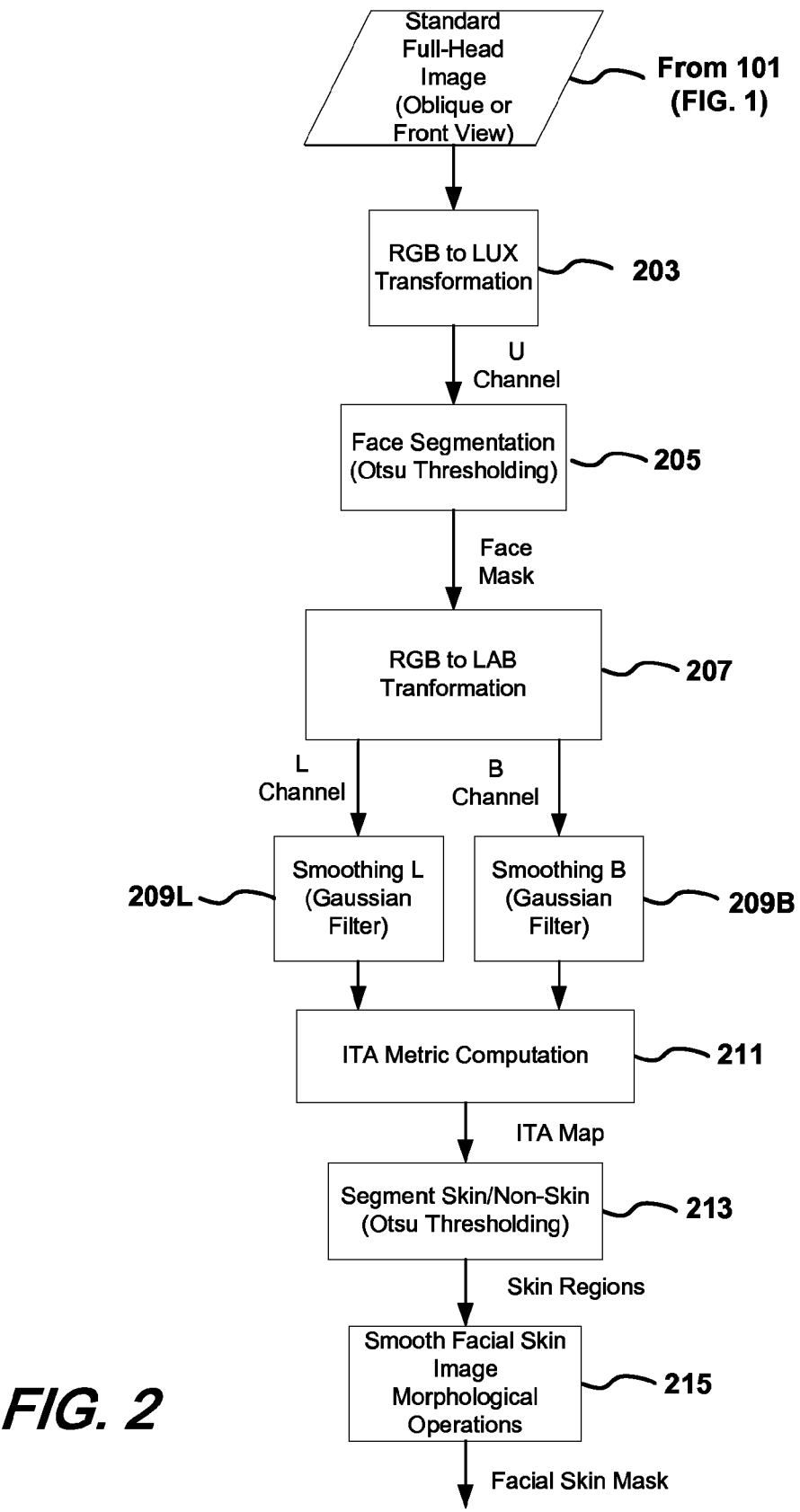
FIG. 2 is a flowchart illustrating an exemplary facial skin detection process, in accordance with the present invention.

FIG. 2 is a flowchart illustrating an exemplary facial skin detection process, in accordance with the present invention, which employs the aforementioned ITA metric. Prior to skin detection, a crude face detection is performed to segment the face region from the overall image which contains the face, hair, neck and background. The detected face region should include all skin regions of face but may also include all the facial features (eyes, eye brows, nostrils, lips, hair). For this purpose, the LUX color space is utilized to segment out the face region from the close-up image. (See M. Levin et al., "Nonlinear color space and spatiotemporal MRF for hierarchical segmentation of face features in video," *IEEE Transactions in Image Processing*, Vol. 13, No. 1, January 2004.)

As shown in FIG. 2, the process begins with the standard, RGB, full-head image, such as provided above at 101. The image is transformed from RGB to LUX space at 203 using a technique described in Levin reference above.

At 205, the face region is segmented out. This can be done, for example, by applying the Otsu thresholding method on the U channel of the LUX image. (See N. Otsu, "A Threshold Selection Method from Gray-Level Histograms," *IEEE Transactions on Systems, Man, and Cybernetics*, Vol. 9, No. 1, pp. 62-66, 1979, hereinafter the "Otsu reference".) A face mask is generated at 205 which delineates the face region. The rest of the facial skin detection process can then be performed only on the face region, thereby reducing the search space and computational cost.

At 207, the original RGB image masked in accordance with the segmentation performed at 205 is transformed into the LAB space. As such, the subsequent ITA metric computation is performed within the face region to further segment out non-skin portions of face. Because the division and inverse tangent operations of the ITA metric computation are sensitive to noise, it is preferable to first smooth the L and B channels. As shown, such smoothing can be done at 209L and 209B, respectively, by filtering the L and B images with 2D Gaussian filters or other similar techniques. The variances of such filters are chosen as 5 for the L channel and 1.5 for the B channel, for a working resolution of 220 PPI.

At 211, the ITA is computed for each pixel within the face region in accordance with the expression: arc tan $((L[i,j]-50)/B[i,j])$. The ITA image is a gray image in the range of [0 90], with smaller values of ITA corresponding to skin pixels and larger values corresponding to non-skin pixels. This gray image is segmented at 213 into two regions using Otsu Thresholding. For this purpose, a histogram of the ITA image is computed only in the face region. Based on the histogram, the Otsu Thresholding algorithm returns a threshold that will segment this image into two classes with minimum inter-class variance. Furthermore, a priori information regarding the ratio of skin regions with respect to overall face image can be incorporated in this thresholding method. (See Q. Hu et al., "Supervised range-constrained thresholding," *IEEE Transactions in Image Processing*, Vol. 15, No. 1, pp. 228-240, January 2006, hereinafter the "Hu reference".) For a typical oblique view image, at least 25% of face pixels should belong to skin pixels. The Hu reference describes how to incorporate this information into the Otsu based segmentation method. After the optimal threshold is computed from the thresholding algorithm, pixels whose ITA values are smaller than this threshold are classified as skin pixels. Thereafter, a binary (black-and-white) image is generated in which skin pixels are shown in white and non-skin pixels are shown in black.

Figure 3C:
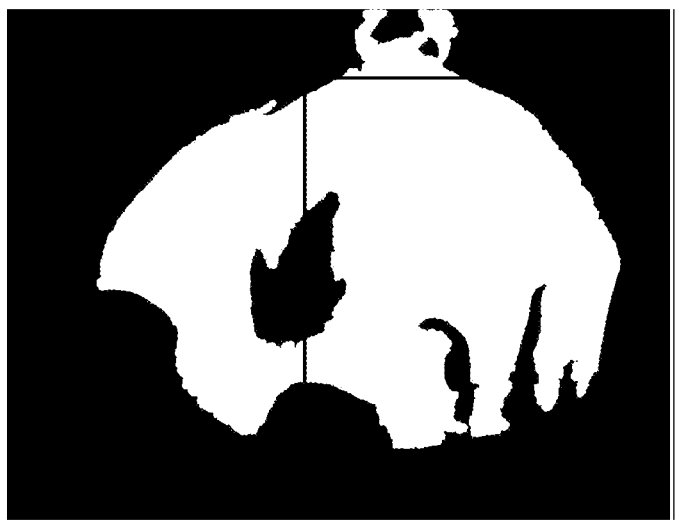
FIG. 3C shows an exemplary texture aging mask (the region below the horizontal black line and to the left of the vertical black line), generated in accordance with an exemplary embodiment of the present invention.
Figure 3B:
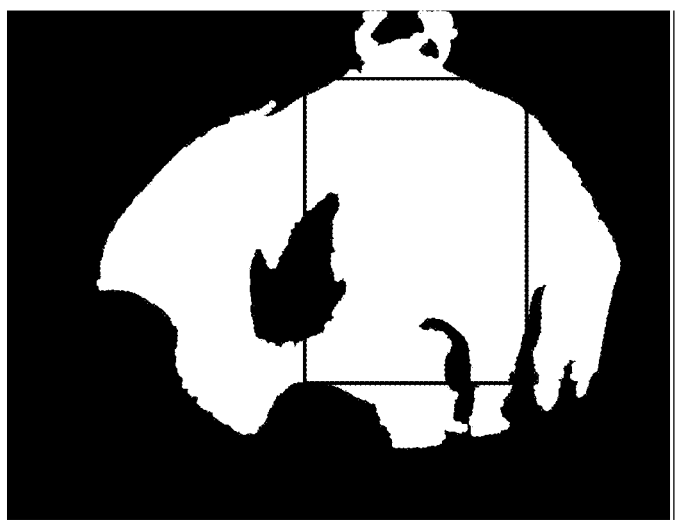
FIG. 3B shows an exemplary spots/wrinkles aging mask (the region within the black lines)
Figure 3A:
FIG. 3A shows an exemplary facial skin mask generated based on a full-face oblique view image.

The segmented skin regions generated at 213 may include isolated non-skin pixels forming small islands. Such non-skin islands may be eliminated at 215 by a morphological closing operation using a disk structural element or other such techniques. The perimeter of this disk is chosen to be 10, for example, for a 220 PPI image resolution. Alternatively, there may be skin patches detected in non-skin facial features (such as eye brows, hair, etc). These small patches are also eliminated by using the morphological opening operation using the same disk structural element. Furthermore, some individuals may have large non-skin patches due to peculiar skin features such as large colored spots. These can also be eliminated by applying the morphological filling operation. The goal is to detect facial skin in one continuous region including cheek, forehead, and nose but excluding nostrils, shadowy nasal labial folds, eye holes, eye-brows, and hair (including any mustache or beard). An example of a valid facial skin mask is shown in FIG. 3A for an oblique view image captured in the VISIA system. Such a facial skin mask is ideal to perform aging simulation in accordance with the present invention.

Design of Aging Simulation Masks

The aging simulation for each skin feature (spots, wrinkles and texture) can be performed on a smaller subset of facial skin regions that is more relevant for that particular aging simulation. For example, performing wrinkles and spots aging simulation on the cheek area (below the eye level and above the lips level) is more effective than doing so in other facial skin regions. For this purpose, as shown in FIG. 1, two different masks—a spots and wrinkles aging mask and a texture aging mask—are generated at 107 based on the full-face skin mask generated at 103. Examples of such masks are illustrated in FIGS. 3B and 3C. These masks are designed based on the eye, lips, and nose locations. The wrinkles and spots mask, shown in FIG. 3B, includes all the skin regions from eyes level to lips level, and from nose-level to end-of-cheek. The texture mask, shown in FIG. 3C, may extend from the eye level down to the end of the chin. The eyes and lips areas are clearly delineated in the full-face skin mask. The locations of these features can be computed by vertical and horizontal projections of this image. One local minimum of the vertical projection provides the center row of the eye, whereas the second local minimum provides the center row of lips. Once these coordinates are determined, the full-face skin image is cropped accordingly to generate the two aforementioned aging simulation masks.

Spots Aging Simulation

Figure 4:
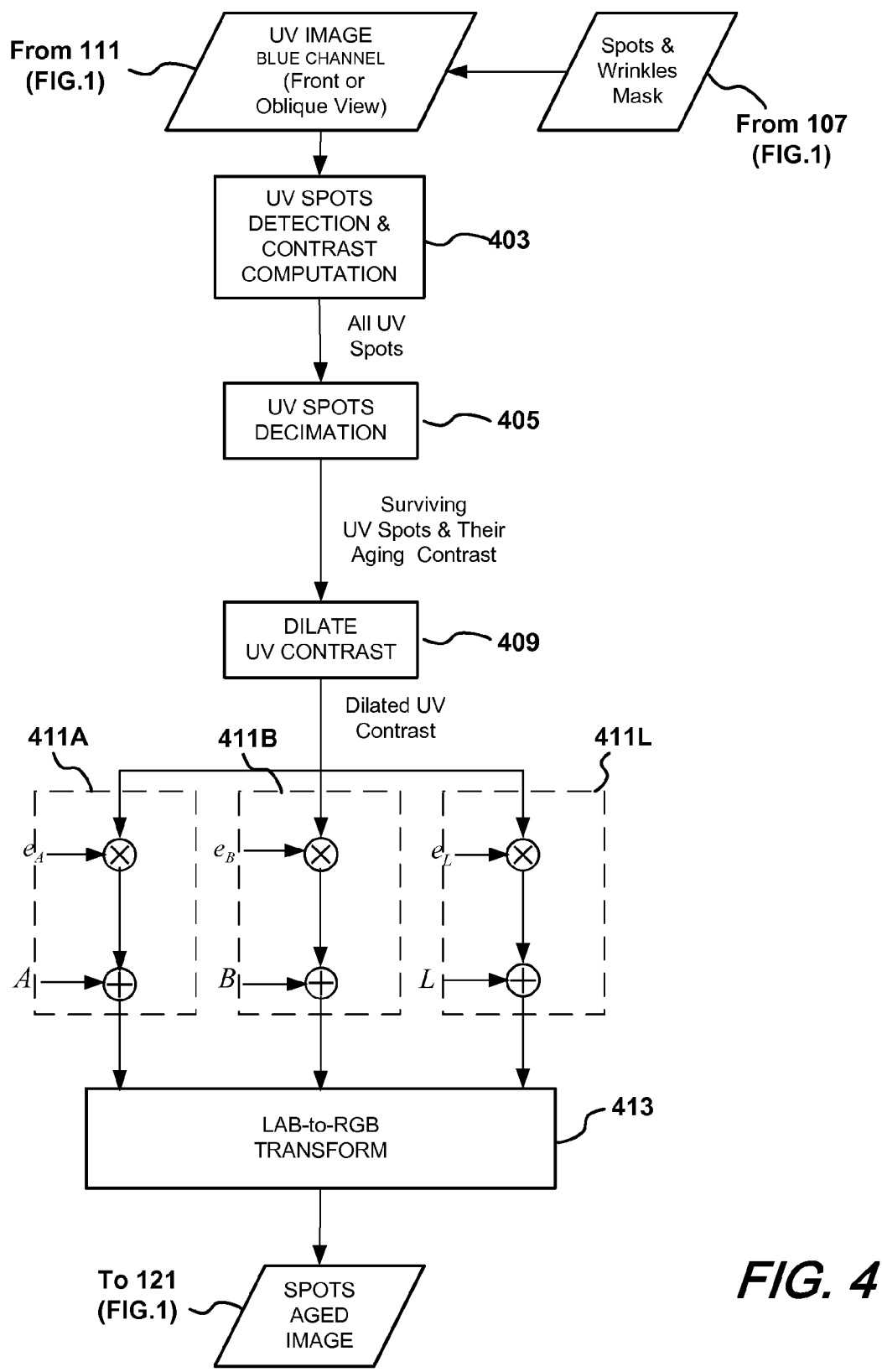
FIG. 4 is a flowchart of a spots aging simulation process in accordance with an exemplary embodiment of the present invention.

FIG. 4 is a flowchart of a spots aging simulation process in accordance with an exemplary embodiment of the present invention. Based on the L*a*b* transformed standard image (from 105, FIG. 1), the UV image (from 111, FIG. 1), and the spots and wrinkles aging mask (from 107, FIG. 1), this process generates the spots aged image. As shown in FIG. 4, the UV image is provided as an input to the spots aging simulation process, along with the spots/wrinkles mask generated as described above. A UV image captured using fluorescent spectroscopy techniques exhibits clearly discernable markers for hyper-pigmented spots. (See the Miyamoto reference.) This lighting modality is commonly used in dermatology to clearly display hyperpigmented lesions that are otherwise not visible in the standard image. There is strong evidence that these hyperpigmented spots, visible only in the UV image, will become visible as the pigmentation worsens, i.e., as melanin deposition increases due to photo-aging. Note that although the exemplary embodiments shown refer to UV images and "UV spots," UV is not the only light spectrum that allows visualization of sub-skin-surface features. In general, this aspect of the present invention is applicable to any sub-skin-surface spots that cannot easily be seen by the unaided eye, regardless of the spectrum of the lighting modality in which they are captured.

The exemplary process of the present invention shown in FIG. 4 simulates the above-described process. The hyperpigmented spots detected from the UV image along with their contrast information can be used to modulate the intensity and color contrast of the corresponding locations in the standard image, thereby simulate the development of "aging spots" with time.

As mentioned above, the standard and UV images ideally should be registered before simulation for optimal realism in display. Capturing the standard and UV images sequentially with a minimal delay, such as with a VISIA system may alleviate, or eliminate the need for registration. Images that are not properly registered, however, can be registered using any of several well-known registration techniques. (See, e.g., B. Srinivasa et al., "An FFT-Based Technique for Translation, Rotation and Scale-Invariant Image Registration," *IEEE Transactions on Image Processing*, Vol. 5, No. 8, August 1996.)

Assuming the images are adequately registered, UV spot detection based on the UV image is performed at 403. An exemplary UV spot detection algorithm in accordance with the present invention is described in detail below. The UV spot detection algorithm returns all the pixel coordinates of UV spots along with their contrast information. The spots are indexed and a specific label (e.g., number) is associated with each spot. The indexing can be done by scanning the black-and-white image representing UV spots row-by-row or column-by-column and assigning a number to each spot in order.

At 405, a UV spot decimation process decimates the adjacent spots in the neighborhood of a spot so that not all the spots in the UV image become visible in the standard image. This decimation process can be justified by the fact that only a subset of all the UV spots will progress to become visible in the standard image. The decimation process can be done by selecting every other or every two other spots in the list of indexed spots. This will provide a sparse subset of all the detected UV spots.

After decimation, the UV contrast image of the surviving spots is generated. The UV contrast image is an intensity image with the UV contrast strength of each pixel in the surviving subset of UV spots. At 409, the UV contrast image of the survived UV spots is dilated to enlarge the UV spots. This will have an enlargement effect on the actual pigmented spots both visible in the standard and UV images. Dilation of the UV spots can be performed by blurring the UV contrast image. This operation can be done by filtering the UV contrast image with a 2D Gaussian filter. The variance of the Gaussian filter for the working resolution is set to 5 and can be increased or reduced to adjust to dilation effect. Alternatively, dilation can be omitted, as it is possible to simulate spot aging without dilation.

At 411A, B and L, the dilated UV spots contrast image is used to modify the luminosity component (L channel) and color components (A and B channels) of the original standard image. The UV spots contrast image is weighted accordingly before being added to the L, A and B components of the original image. As is known, the effect of pigmentation is visible in the L, A and B channels with varying degrees of strength. In an exemplary embodiment, the UV spots contrast is multiplied by 1.5 before being added to the L channel (i.e., $e_L=1.5$), by −0.5 before being added to the A channel, and by −0.5 before being added to the B channel (i.e., $e_A=e_B=-0.5$). The signs and absolute values of these numbers are determined based on research findings and empirical observations. After adding the aging contrasts, the spots aged image is synthesized by performing an LAB-to-RGB transformation at 413. Note, as mentioned above, the present invention is not limited to any particular color or image format. For example, if the resultant image is to be printed, the transformation at 413 may be a LAB-to-CMY transformation (i.e., to the well-known cyan-magenta-yellow color space typically used in printing). As can be appreciated, the images generated by the present invention may be displayed, printed, stored, transmitted, or subjected to any further processing. Moreover, as can be appreciated, the transformation at 413 can be dispensed with or deferred if, for example, the resultant image is to be stored or transmitted in the LAB format.

As such, the aging simulation is done in the LAB domain by intelligently adding factors of the UV contrast information into the intensity (L) and color (A and B) components. Hyperpigmentation is extensively studied and quantified in the LAB domain often with calorimeters (S. Alaluf et al., "The impact of epidermal melanin on objective measurements of human skin colour", *Pigment Cell Research*, Vol 15. pp: 119-126, 2002, hereinafter the "Alaluf reference") and analyzing the image in the LAB domain (N. Kollias et al., "Optical Non-invasive Approaches to Diagnoses of Skin Diseases," *Journal of Investigative Dermatology Proceedings*, Vol. 7, No: 1, pp: 64-75, 2002). One research study involving the color measurements of normal and hyperpigmented regions of human skin with an LAB choromameter indicates that all L, A, and B values vary with the degree of pigmentation (melanin content). (See Alaluf reference.) It is reported that L values will be smaller with increased melanin content, while A and B values will be increased with melanin content. This explains the dark brown look of hyperpigmented spots.

UV Spot Detection and Contrast Computation

Figure 5:
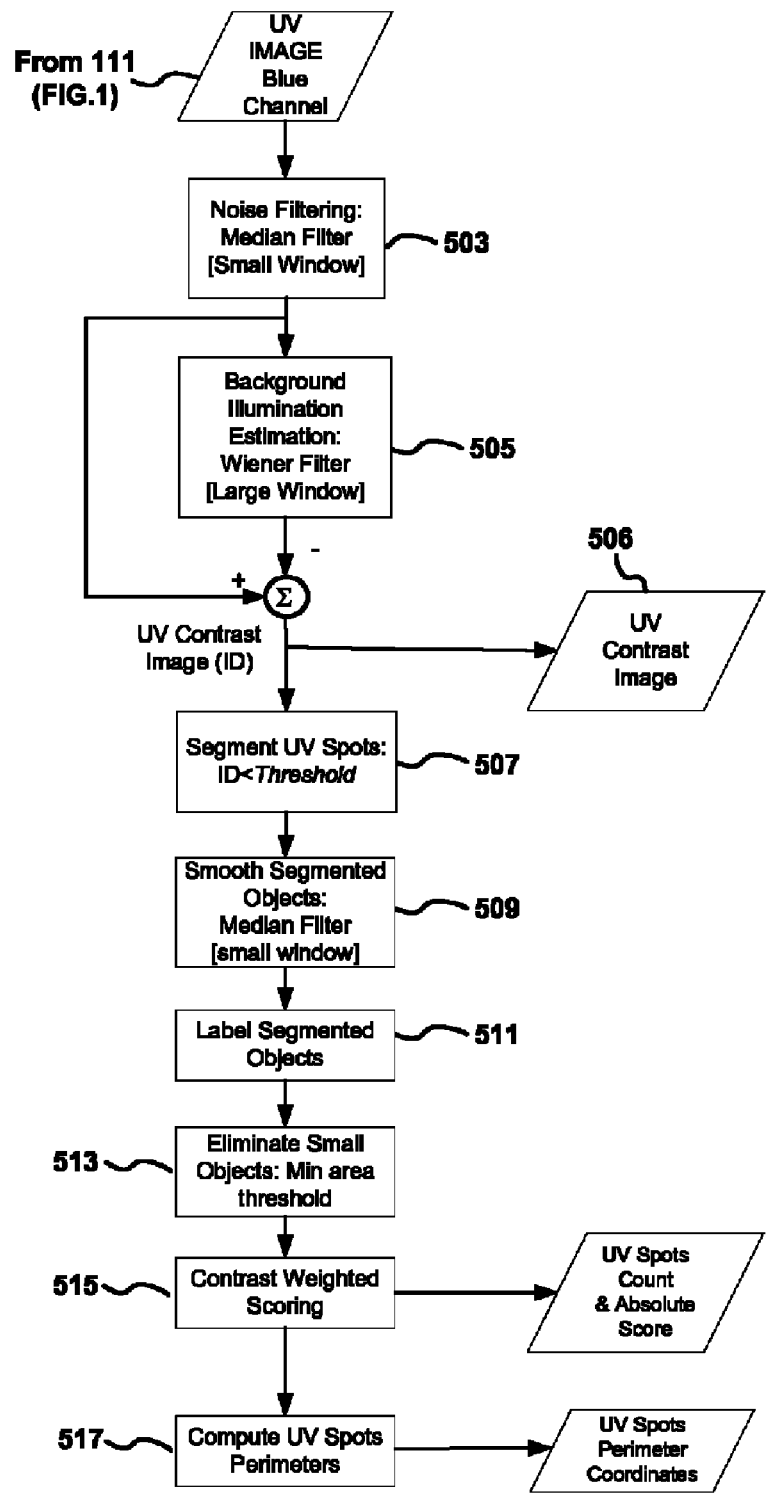
FIG. 5 is a flowchart of an exemplary process of detecting UV spots and computing contrast in accordance with the present invention.

FIG. 5 is a flowchart of an exemplary process of detecting UV spots and computing contrast. This process takes the blue channel of the aforementioned UV image (such as from 111, FIG. 1), and returns the UV spots along with the UV contrast image. The blue channel of the UV image exhibits the best contrast among the channels (R, G and B) because the UV florescence is stronger in the blue spectrum. The goal of the process of FIG. 5 is to extract UV spots lesions from this gray intensity image.

At 503, the blue channel UV image is subjected to noise filtering in which small variations in the image are smoothed. For this purpose, a [5×5] median filter has been found to be effective for the UV image (with a working resolution of 220 PPI.) Because of the non-uniform strength field of the light source and the three-dimensional shape of the face, not all of the image pixels receive an equal amount of light, hence contributing to an image with varying degrees of intensity at different regions of the face. This variation in intensity prohibits the use of a fixed threshold to segment out the UV spots lesions that are visibly darker than the background. To compensate for non-uniform intensity, a slowly varying background intensity is estimated at 505 and removed from the filtered intensity for each pixel. The slowly varying background intensity can be estimated by utilizing a local low-pass filter with a large filter support. Such a filter can be implemented using a Wiener filter, i.e., an adaptive low-pass filter that estimates the low frequency 2D intensity surface based on the local mean and local variance. An exemplary Wiener filter that can be used for this purpose is described in Appendix A-1 by a set of image pixel update equations. The support (size) of the Wiener filter is chosen, for example, as [41×41], large enough to encapsulate an average large size UV spot, assuming a working resolution of 220 PPI.

When the background intensity level is removed from the noise-filtered version of the original intensity image, a contrast image is obtained. This contrast image includes both positive and negative components. UV spots lie in a subset of the negative contrast regions. Hence, at 507, UV spots are obtained by segmenting the negative contrast image by a fixed threshold. In an exemplary embodiment, this threshold is chosen to be in the range of approximately −3.5 to −5.0. The criterion for a UV spot is that its contrast value should be smaller than this threshold. This spot segmentation agrees well with an average human perception.

As a result of the segmentation operation at 507, a binary (black-and-white) image is obtained where white lesions represent the UV spots and black pixels represent the background. This image is smoothed at 509, such as with a [5×5] median filter. At 511, the UV spots are indexed and labeled, and the area (e.g., number of pixels) associated with each UV spot is computed. At 513, small UV spots whose areas are less than a threshold (e.g., 150 pixels) and large UV spots whose areas are greater than a threshold (e.g., 600 pixels) are eliminated. The surviving UV spots are returned along with the contrast values for each pixel, i.e., UV contrast image generated at the process 506. It is important to recall that these contrast values are negative and represent the dark contrast. Optionally, a severity score is generated based on the UV contrast image (ID) by contrast weighted scoring at 515. This score is computed by summing all the ID values within the valid UV spots. This score is associated with the degree of hyperpigmentation and can be used to monitor worsening or improvement of pigmentation. Furthermore, the detected UV spots perimeters are computed at 517 so they can be overlaid on the UV image to display the UV spots.

Spots De-Aging Simulation

In an exemplary embodiment, spots de-aging simulation is performed in the LAB color space utilizing the L, A, and B channels of the standard image. Along with hyperpigmented spots, red spots (small areas of inflammation due to scarring and skin diseases such as acne) are discernible in these channels. For more realistic simulation, such colored skin features are preferably removed in accordance with an exemplary embodiment of the present invention.

Figure 6:
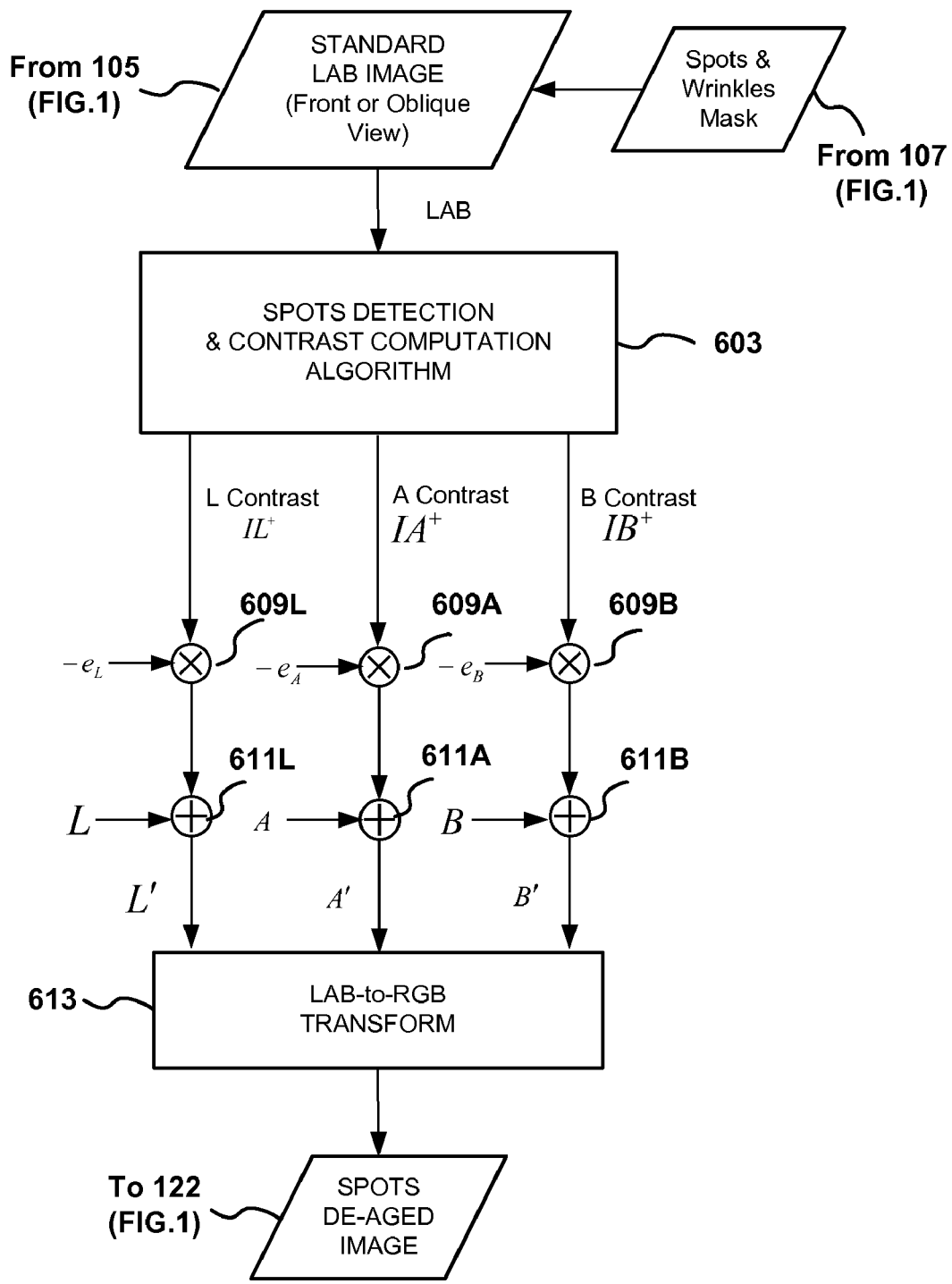
FIG. 6 is a flowchart of an exemplary spot de-aging process in accordance with the present invention.

FIG. 6 is a flowchart of an exemplary spot de-aging process in accordance with the present invention. Using the LAB image (such as from 105, FIG. 1) and the spots and wrinkles mask (such as from 107, FIG. 1), spot detection and contrast computation are performed at 603. An exemplary spot detection and contrast computation algorithm is described in detail below with reference to FIGS. 7A and 7B. Contrast refers to the differential intensity of the pixel with reference to the low-pass background intensity computed from the local neighborhood.

The contrast values in L within the spot lesions are multiplied at 609L by a value $e_L$ and added to the to the original L channel at 611 to level the negative contrast in L with the background level. Similarly, the contrast values within the spot lesions in A are multiplied at 609A by a value $e_A$ and added to the to the original A channel at 611A to level color difference in A with the background color. Similarly, the contrast values within the spot lesions in B are multiplied at 609B by a value $e_B$ and added to the original B channel at 611B to level color difference in B with the background color. Note that the contrast in L is used to modify the darkness of spots whereas the contrasts in A and B are used to modify the color of spots. The removal of contrasts in the L, A, and B channels within the spot lesions will make the intensity and color of spots lesions leveled with the intensity and color of the background skin. This will have a visual effect of removed spot lesions, and smoother appearance of facial skin. Therefore, the spots de-aged image can be used to foresee the results that could be expected with an effective treatment.

Spot Detection Algorithm

Figure 7A:
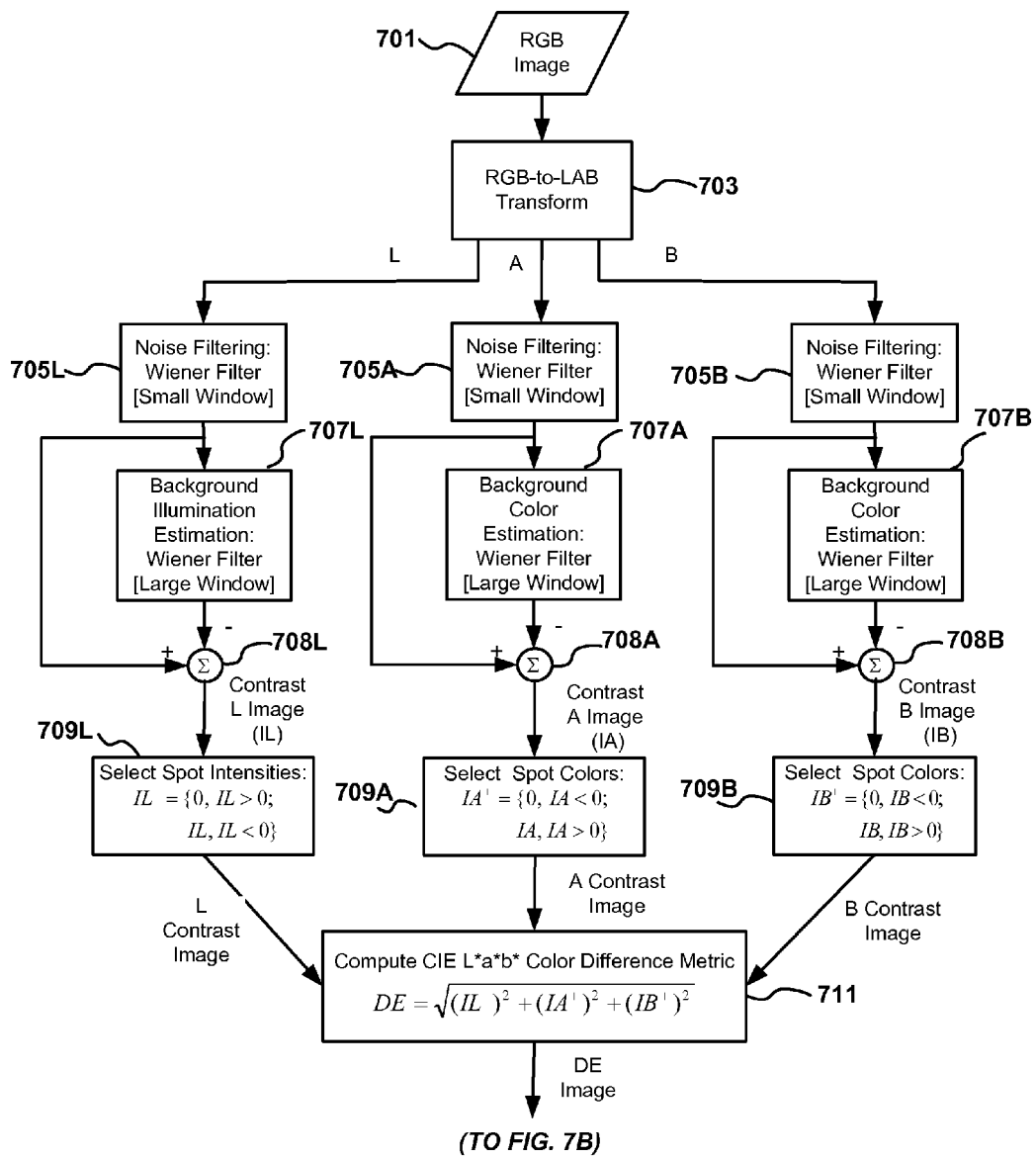
FIGS. 7A and 7B show a flowchart of an exemplary Spot detection algorithm in accordance with the present invention.
Figure 7B:
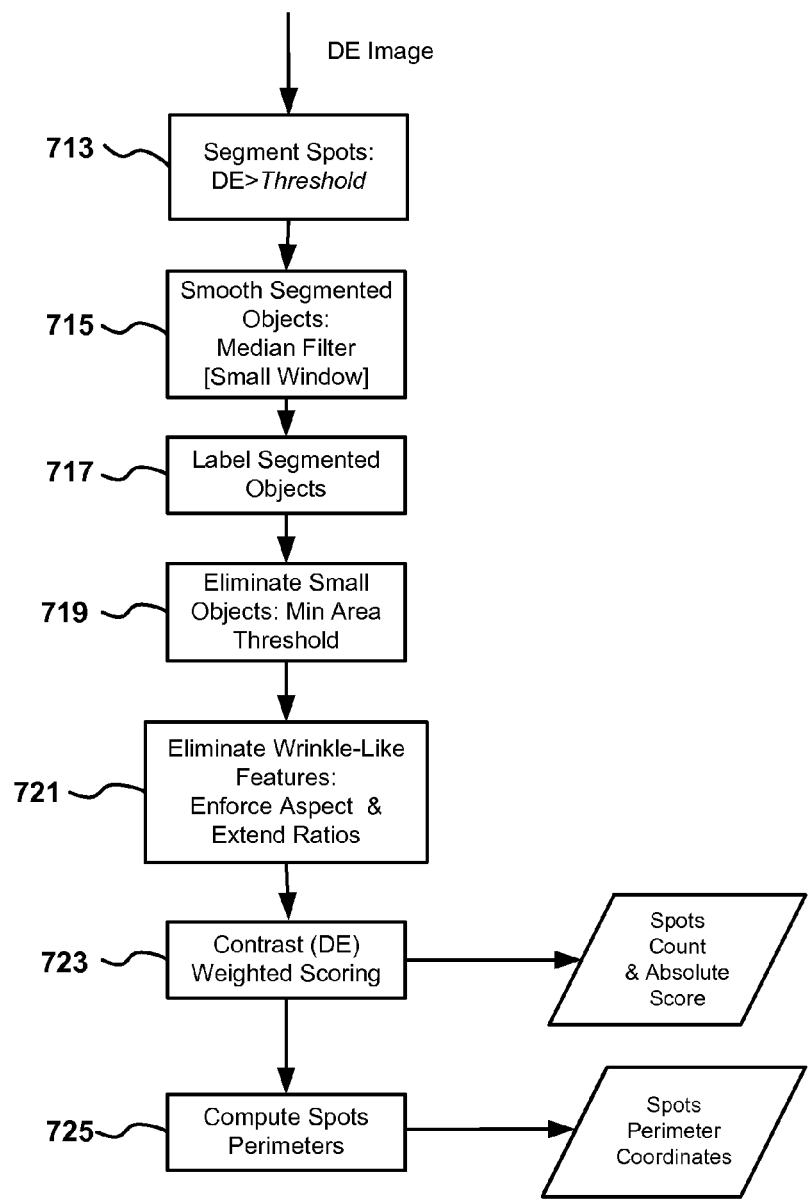

An exemplary Spot detection algorithm is illustrated in FIGS. 7A and 7B. At 703, the standard RGB image 701 is transformed into the LAB color space, and noise filtering is individually applied to the L, A, and B channels at 705L, 705A and 705B, respectfully. In the exemplary embodiment shown, noise filtering is performed with a Wiener filter, as described above, with a smaller filter support, e.g., [5×5]. Then, at 707L, 707A, and 707B, Wiener filters with a support of e.g., [61×61] are applied to the noise filtered L, A, and B images, respectfully, to estimate the background intensity and color for each pixel in the spots and wrinkles simulation mask. The contrast values are computed for each pixel of the L, A and B channels by subtracting, at 708L, 708A, and 708B, respectively, the low-pass L, A, and B values for each pixel from the noise filtered L, A and B values for each pixel.

The contrast images (where "contrast image" refers to the collection of all image pixels with contrast values as intensity) are good indicators of spots. It is well established in dermatology research that the intensities of spot lesions are smaller than the intensity of background skin, and their color components in A and B are larger than the color readings of background skin. (Note that background skin is considered healthy and smooth here, and spot lesions are considered sparse within the background.) Based on these criteria, spots lesions are selected in the negative contrast regions in channel L and positive contrast regions in channels A and B, at 709L, 709A, and 709B, respectively. Furthermore, the contrast images obtained from 708L, 708A, and 708B are refined to produce more meaningful contrast images by 709L, 709A, and 709B operations. The contrast images after these operations are used for de-aging simulation of spots.

At 711, a spots color difference metric (DE) is computed for each pixel based on the contrast values from the L, A and B channels. The CIE L*a*b* perceptual color difference metric is often used in color science to quantify the sensitivity of human vision to differentiate between two color patches. In the exemplary embodiment, this metric was adopted to differentiate a spot color from the background skin color so that spot segmentation is in agreement with human perception. Generally, if this metric is larger than 3.5 an average eye can tell the difference in color.

Proceeding to FIG. 7B, spot segmentation is performed at 713 by comparing DE to a threshold, e.g., 4.5, to segment out spots. This threshold can be changed from 3.5 to 5 based on the desired sensitivity. After this thresholding operation, a binary (black-and-white) image of spot lesions is obtained where white islands represent spots. This binary image is optionally smoothed at 715 to have smooth shaped spot lesions.

At 717, the segmented objects are labeled by assigning numbers.

A spot segmentation procedure based on thresholding DE, such as described above, will generally segment out portions of wrinkles and a subset of large pores along with the spots. At 719, small objects, such as pores, which are generally smaller than spots, are eliminated by applying a minimum area constraint to the segmented objects. For example, an area threshold of 100 pixels at the specified resolution (220 PPI) is satisfactory.

At 721, in order to eliminate wrinkles and wrinkle-like features, certain shape properties of the remaining spot lesions are then computed. Exemplary properties may include area, aspect ratio, solidity, major-axis-length, minor-axis-length, eccentricity, and extent. These are 2D shape properties commonly used in the art and defined in Appendix A-3, Definitions of Shape Properties. To eliminate wrinkles and wrinkle-like features, the aspect ratio (minor-axis-length/major-axis-length) is used as a criterion. An object with an aspect ratio less than 0.25, for example, could be deemed a wrinkle and eliminated as a spot. Also an extent threshold of 0.3, for example, can be used to eliminate deformed and fuzzy shape features. (Extent is a measure of compactness that varies in the range [0 1] with high values corresponding the compact objects.) After these shape and size constraints are applied at 721, the surviving objects and their pixel locations are recorded along with the contrast values previously computed at 709L, 709A, and 709B for these spot locations. The contrast values are used for de-aging simulation of spots. Optionally, a severity score is generated at 723 based on the overall contrast image (DE) computed at 711. This score is computed by summing all the DE values within the valid spots. This score is associated with the degree of hyperpigmentation and unevenness of skin and can be used to monitor worsening or improvement of skin condition. Furthermore, the detected spots perimeters are computed at 725 so they can be overlaid on the image to display the spots.

Wrinkles Aging and De-Aging Simulation

FIG. 8 is a flowchart of an exemplary wrinkle aging and de-aging simulation process in accordance with the present invention. At 801, a wrinkle detection procedure is performed using the luminosity (L) channel of the LAB image as masked by the spots and wrinkles mask generated above. A color analysis of wrinkle features demonstrates that the color in wrinkle lines is not visibly different from the color of the background skin. The intensity of wrinkles, however, is visibly different than the background intensity. As such, the L channel is used to detect and simulate wrinkles aging/de-aging. The wrinkle detection procedure at 801 provides wrinkle features along with their "wrinkle strength" values. "Wrinkle strength" is a different measure than wrinkle contrast and is computed based on directional filters. (See W. T. Freeman et al., "The design and use of steerable filters," *IEEE Trans. Pattern Analysis and Machine Intelligence*, Vol. 13, Vo. 9, pp. 891-906, 1991, hereinafter the "Freeman reference.") An exemplary wrinkle detection algorithm is described below in detail.

Wrinkle detection is followed by a false wrinkle elimination procedure at 803. The wrinkle candidates generated by the wrinkle detection procedure at 801 are segmented out as white objects on a dark skin background. This black-and-white image is called a ridge-objects image. The majority of ridge objects are due to wrinkles and small creases but some may come from other facial features such as, for example, the borders of large spots, aligned pores, dark hair on skin, and spider veins, among others. Most of these false features can be eliminated based on a set of shape, size and color criteria. An exemplary process for doing so is described below in greater detail. This process returns the valid wrinkles along with their strength image. The wrinkles strength image takes the value of the ridge map on valid wrinkles pixels and zero elsewhere. This wrinkles strength image will be used for wrinkle aging and de-aging simulation.

For aging simulation of wrinkles, the wrinkle strength, hereafter called wrinkles contrast, is dilated at 807 to get a thickening effect which will occur overtime with aging. The dilation operation can be performed, for instance, with a 2D Gaussian filter with a filter variance of 2, for example. This procedure is described above with respect to UV spots dilation. At 809A, the dilated contrast is then multiplied by an enhancement factor $e_L$ (e.g., 2) and added to the L channel. The net effect of these operations is that wrinkles seen in the original image appear darker and thicker, and weak wrinkles not clearly visible in the original image become visible. Finally, the wrinkle-aged image is then synthesized by an LAB-to-RGB transformation at 811. It is important to note that wrinkles will grow with age, and the simulation of this process can be done by extending the detected wrinkles. The extending of the wrinkles may be done in addition to or alternatively to the dilation operation.

For the de-aging of wrinkles, contrast dilation is not performed and at 809D, the wrinkle contrast is removed from the L-channel so that the intensity level of the wrinkle is brought to the intensity level of the surrounding background skin. Finally, the wrinkle de-aged image is synthesized by an LAB-to-RGB transformation at 813.

Wrinkles Detection Algorithm

Figure 9:
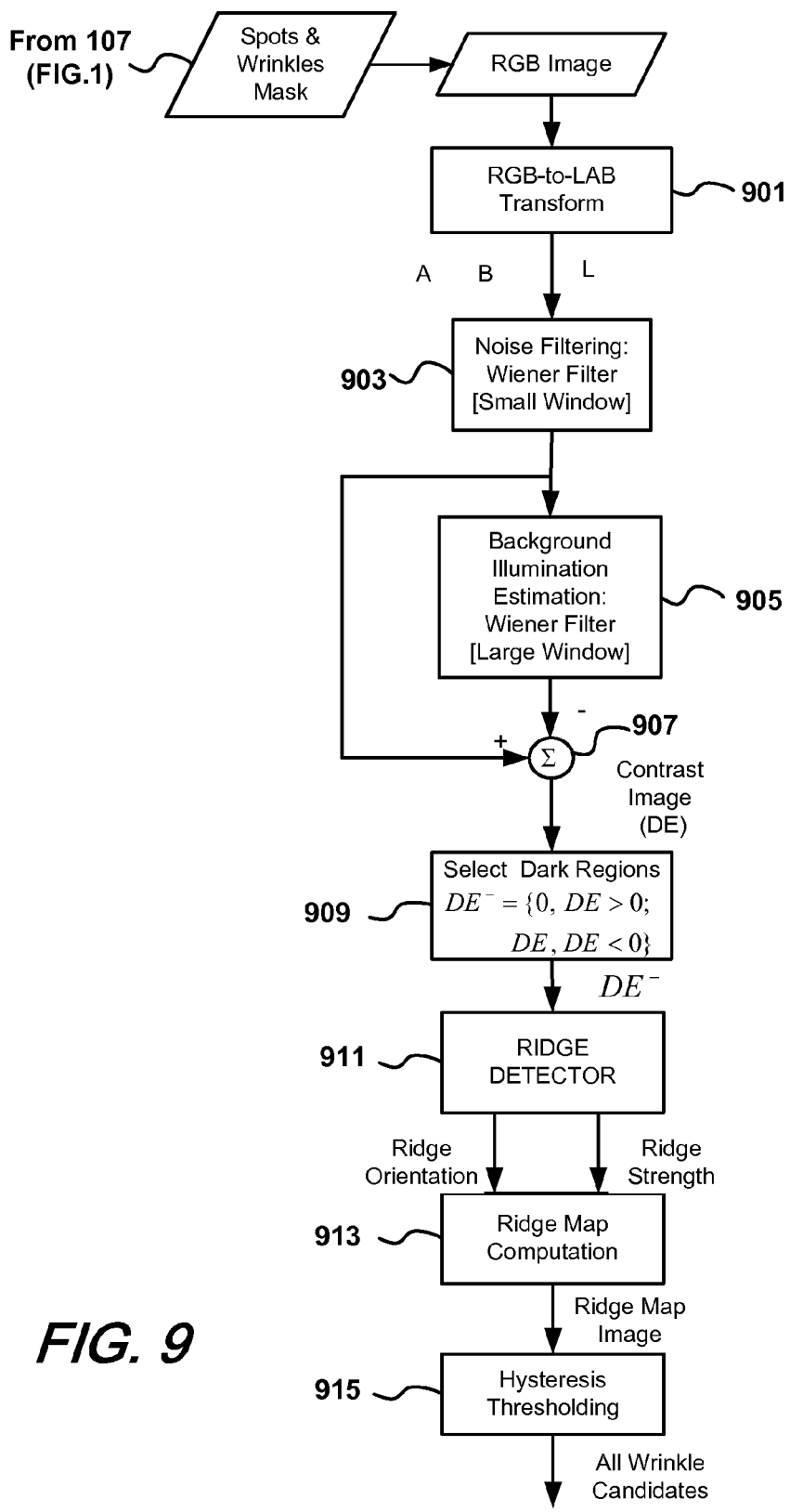
FIG. 9 is a flowchart of an exemplary wrinkle detection process in accordance with the present invention.

A wrinkle detection process will now be described with reference to FIG. 9. At 901, the standard RGB image masked by the spots and wrinkles mask is transformed to obtain the LAB image. In the exemplary embodiment, only the L channel is used to detect wrinkles. At 903, a noise filtering process using a Wiener filter, as described above, is applied to the L channel within the wrinkle aging simulation mask. The filter has a support of e.g., [3×3]. At 905, a further Wiener filter with a support of e.g., [21×21] is applied to the noise filtered L channel to estimate the background illumination intensity. Preferably, the size of this filter should be large enough to cover wrinkles in the working resolution. The contrast values are computed at 907 for each pixel by subtracting the low-pass L value from the noise filtered L value within the wrinkles mask.

At 909, the regions with negative contrast values (i.e., the dark regions) are selected for wrinkle detection. This is based on the observation that wrinkle lines are darker (lower in L) than the background. At 911, a ridge detection procedure is applied to the negative contrast image to detect elongated structures. In an exemplary embodiment, described in greater detail below, the ridge detection procedure uses directional filters (see Freeman reference; and J. Staal et al., "Ridge-based segmentation in color images of retina," *IEEE Transaction on Medical Imaging*, Vol. 23, No. 4, pp. 501-509, April 2004, hereinafter the "Staal reference.") The ridge detection procedure accepts the contrast image and returns a "ridge strength" and a "ridge orientation" image. These two images are further processed at 913 to achieve a modified ridge strength image, or "ridge map." A ridge map computation procedure is described below in detail. The ridge map is a gray intensity image that represents curvilinear structures and exhibits a strong response to wrinkles.

To determine the wrinkle structures from the ridge map image, hysteresis thresholding (see F. J. Canny, "A computational approach to edge detection", IEEE Transactions on Pattern Analysis and Machine Intelligence, Vol. 8, No. 6, pp. 679-698, 1986) is applied at 915. Hysteresis thresholding is a softer form of thresholding that connects weak structures to strong structures and involves a low and a high threshold. Exemplary values for these thresholds are 4 and 8.

Ridge Detection

Wrinkles manifest themselves as elongated structures in the standard image. They are most visible in intensity (L channel) with respect to background skin intensity level and hardly differentiable in terms of color (A and B channels) compared with background skin color. Hence they can be extracted from the L channel by utilizing a detector designed for elongated structures.

Figure 10:
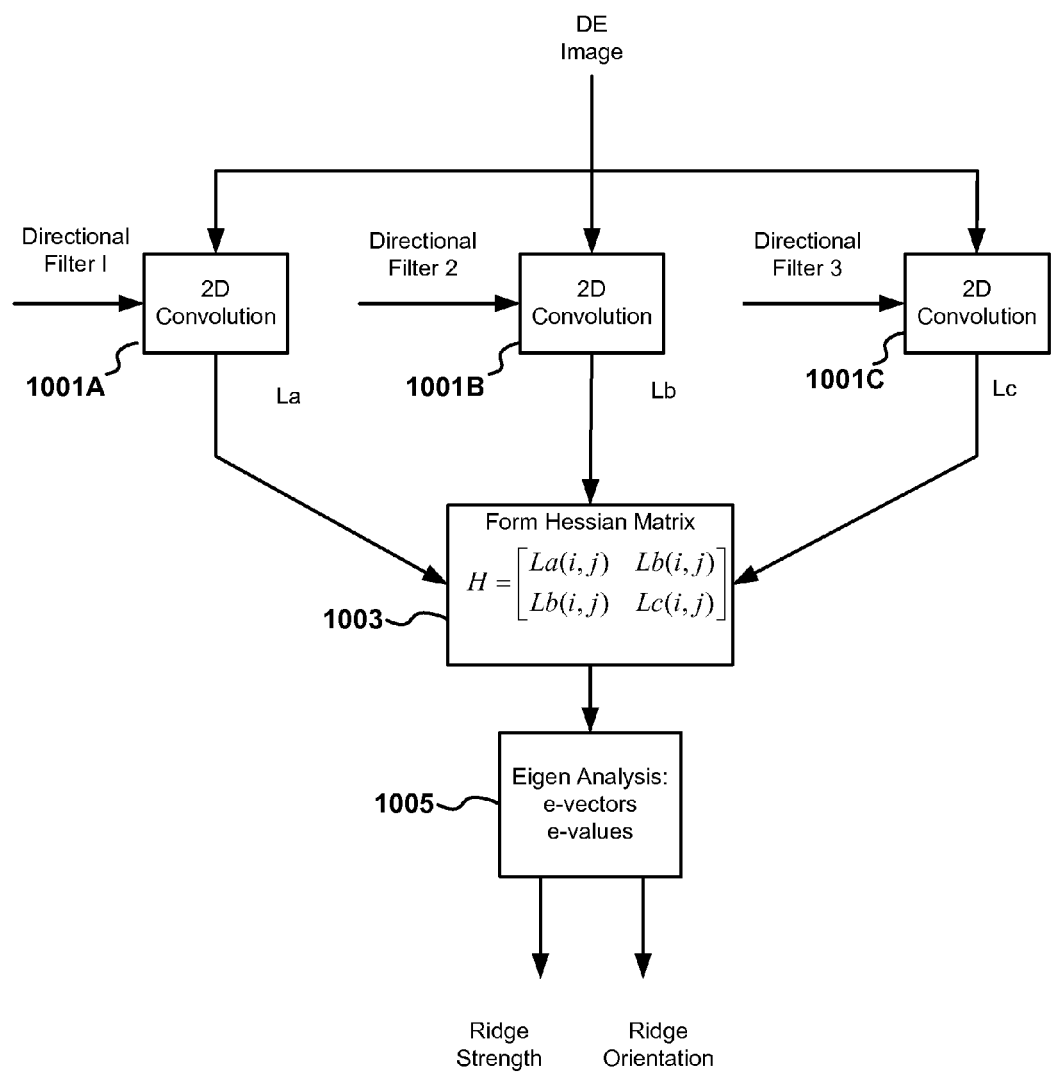
FIG. 10 is a flowchart of an exemplary ridge detection process in accordance with the present invention.

The second order directional derivatives of the Gaussian kernel are commonly used to detect elongated structures in image processing. (See, e.g., the Staal reference. These derivatives are actually a class of steerable filters described by the Freeman reference.) These are basis filters sensitive to ridge features and have vertical, horizontal and diagonal orientations. FIG. 10 is a flowchart of an exemplary ridge detection procedure which utilizes such steerable filters.

As shown in FIG. 10, the DE image is subjected at 1001A, 1001B and 1001C, respectively, to a two-dimensional convolution with a first, second and third directional filter, such as described above. In order to analyze the orientation and strength of a structure in an image, a Hessian matrix is formed at 1003 for each pixel whose elements are the basis filter responses. Then, at 1005, an Eigen analysis is performed on the [2×2] Hessian matrix for each pixel. Eigen analysis returns two eigen-values (e1, e2) and two eigen-vectors (v1, v2) orthogonal to each other. Ridge strength is defined as the positive eigen-value (e.g., e1) if its absolute value is greater than the second eigen-value (e.g., e2), and ridge orientation is the second eigen-vector (v2). In one variation of this method, the ridge strength is defined as (e1-e2) when e1>0 and |e1|>|e2|. It has been observed that this definition emphasizes wrinkle structures better.

Ridge Map Computation

As described, the exemplary ridge detection process returns two useful parameters for each pixel: ridge strength, a scalar value indicative of how deep a wrinkle is; and ridge orientation, a vector which specifies the direction of a wrinkle at a particular pixel location. A ridge map image is generated based on these two parameters. In doing so, a new ridge strength is defined for each pixel which takes into account the original ridge strength, and a strength term depending on the orientations of the neighboring pixels. This strength term is computed by summing the inner products of the direction vector of the current pixel with the direction vector of each of the pixels in the 8-connected neighborhood of the current pixel. This process is described by a set of equations in Appendix A-2.

False Wrinkle Elimination

The aim of the false wrinkle elimination process is to eliminate false positives (false wrinkles) based on shape, and size properties. For this purpose, all of the wrinkle candidates after Hysteresis thresholding (915) are labeled and a number of shape properties are computed for each. These shape properties may includes: minor-axis-length, major-axis-length, area, solidity, and eccentricity. The definitions of these 2D shape properties are standard and given in Appendix A-3.

Based on these shape properties, the ridge-objects are classified into four categories: short wrinkles, long wrinkles, network wrinkles, and non-wrinkles. To fall within one of first three categories, a ridge-object's properties must meet a corresponding set of criteria. For example, for a ridge-shape to be a short wrinkle, its length must be between the minimum (e.g., 30 pixels) and maximum length (e.g., 50 pixels) thresholds; its aspect ratio (minor-axis-length/major-axis-length) must be smaller than an aspect threshold (e.g., 0.25); its eccentricity must be greater than an eccentricity threshold (e.g., 0.97), and its solidity must be greater than a minimum solidity threshold (e.g., 0.49). Similarly, there is a set of criteria for long wrinkles and another set of criteria for network wrinkles. These thresholds are empirically determined based on the inspection of wrinkles on a set of training images. The ridge-objects not classified as one of these wrinkle types are classified as non-wrinkles. The remaining ridge-objects are called valid wrinkles and returned to the wrinkle detection algorithm.

Texture Aging Simulation

The term "texture" is used herein to refer to small skin features disturbing the overall smoothness of skin. Texture aging and de-aging simulation is based on the detection of texture features and contrast. Texture features include pores, small white colorations, and small rough perturbations. Texture aging and de-aging simulation is performed within the texture mask. A typical texture mask is illustrated in FIG. 3C.

Figure 12:
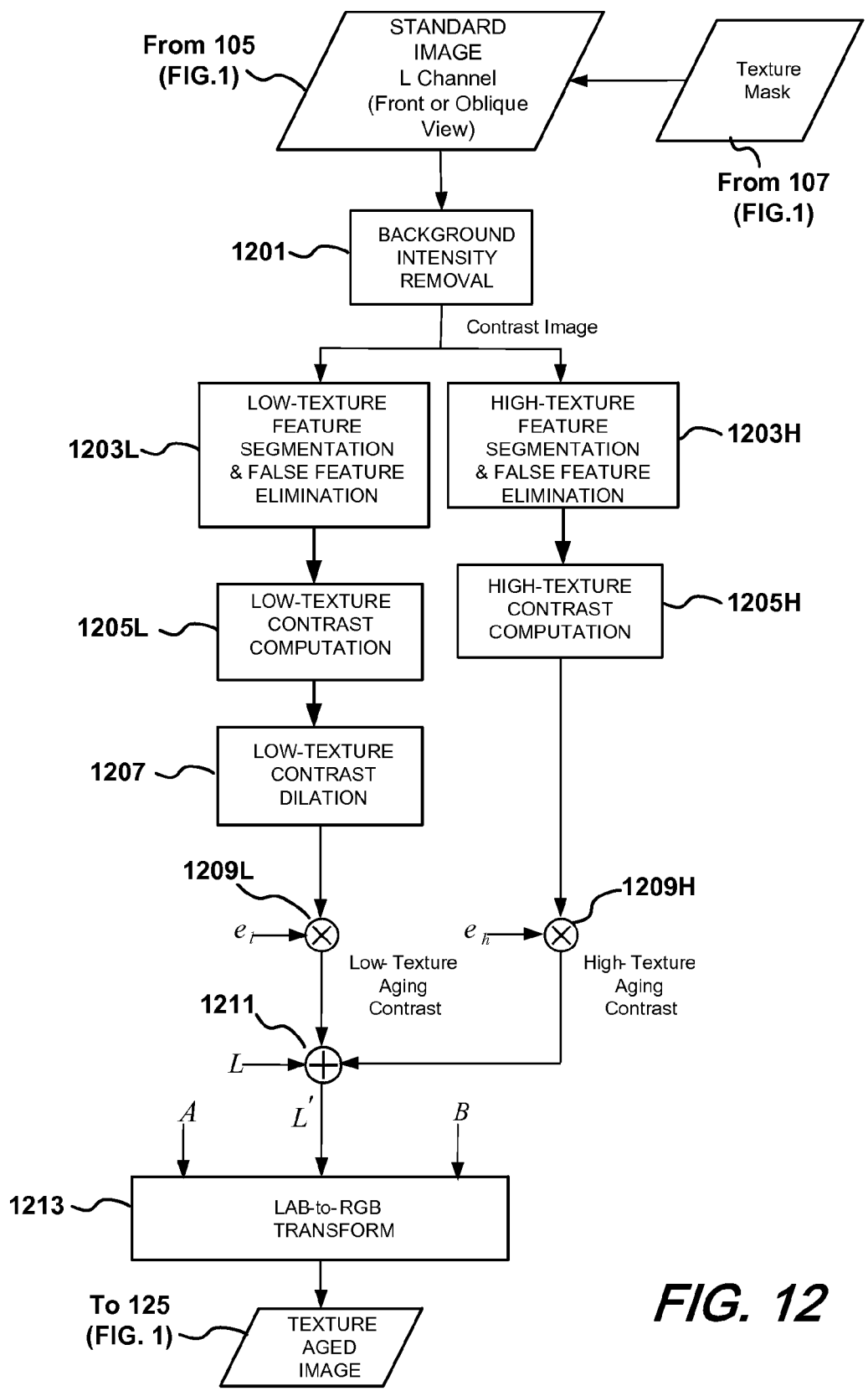
FIG. 12 is a flowchart of an exemplary texture aging process in accordance with the present invention.

FIG. 12 is a flowchart of an exemplary texture aging process in accordance with the present invention. Texture aging simulation is performed using the Luminosity (L) channel of a standard facial image (such as that from 105, FIG. 1) masked by a texture mask (such as that from 107, FIG. 1). At 1201, removal of low-pass background intensity from the L channel takes place. For this purpose, the background intensity level is computed by applying a Wiener Filter, such as described above, with a filter support of e.g., [21×21]. This term is subtracted from the L channel to generate the contrast image. The contrast image has both negative and positive components. The regions with negative contrast values are called low-texture regions, and the regions with high contrast values are called high-texture regions. Examples of low-texture regions are pores, whereas examples of high-texture regions are very small white spots.

Segmentation of the low-texture regions takes place at 1203L by thresholding the negative contrast image with a negative threshold (e.g., −2.5), i.e., by selecting pixels whose contrast is less than this threshold. Furthermore, the segmented texture lesions are labeled and the areas of lesions are also recorded. A small area threshold (e.g., 10) is applied to remove very small lesions, primarily due to noise. A large area threshold (e.g., 120) is applied to remove large lesions that are due to small spots and wrinkles.

The remaining texture lesions and their contrast values for each pixel (low-texture contrast image) are recorded at 1205L. Furthermore, the low-texture contrast image is dilated at 1207, such as by using a 2D Gaussian filter with a variance value of 1. The net effect of this dilation operation is the enlargement of pores in the facial image. Pores enlargement naturally occurs with age, or by worsening of skin health. The variance value can be increased to increase the degree of enlargement.

Similarly, for segmenting the high-texture regions, a positive threshold (2.5 typical) is applied to the positive contrast image at 1203H, i.e., by taking pixels greater than this threshold. Then, the segmented texture lesions are labeled and the areas of lesions are recorded. A small area threshold (typical 10 pixels) is applied to remove very small lesions primarily due to noise. A large area threshold (typical 100 pixels) is applied to remove large lesions that are due to shine, i.e., excessive light reflections on the face. The remaining texture lesions and their contrast values for each pixel are recorded at 1205H.

At 1209L, the dilated low-texture contrast is multiplied by an enhancement factor $e_l$ and added to the L channel at 1211. Similarly, the high-texture contrast image is multiplied by an enhancement factor $e_h$ and added to the L channel at 1211. Exemplary values for the enhancement factors $e_l$ and $e_h$ are 1.0 and 0.5, respectively. At 1213, the texture-aged image is synthesized by an LAB-to-RGB transformation.

Texture De-Aging Simulation

An exemplary texture de-aging simulation is aimed at reducing the size and intensity of texture features such as pores and small white spots. Completely removing texture features as in spots or wrinkles de-aging simulations will cause an over-smoothed appearance and does not provide a realistic skin image.

Figure 13:
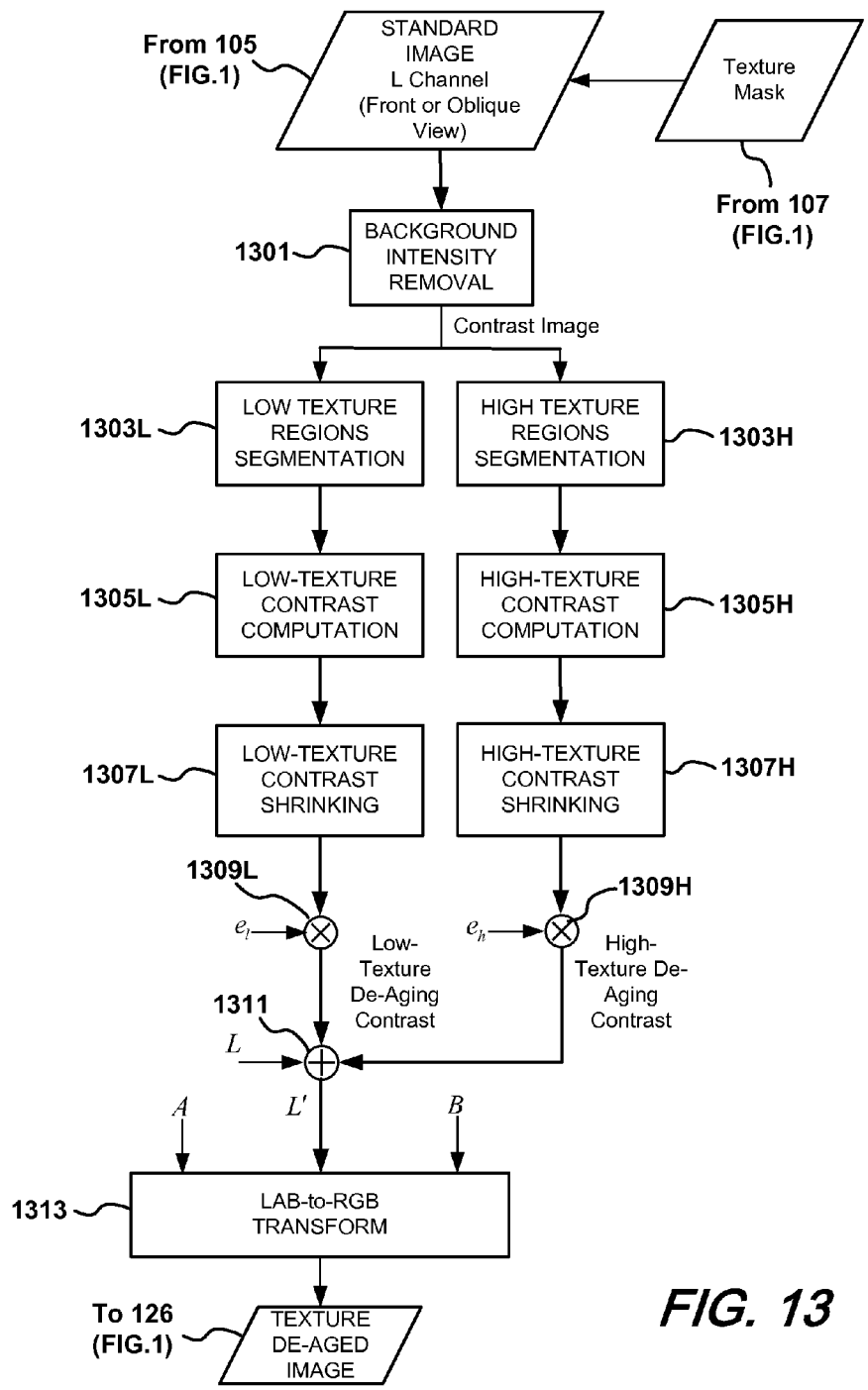
FIG. 13 is a flowchart of an exemplary texture de-aging process in accordance with the present invention.

FIG. 13 is a flowchart of an exemplary texture de-aging process in accordance with the present invention. Texture de-aging is also performed in the Luminosity channel. At 1301, the removal of the low-pass background intensity from the L channel takes place. For this purpose the background intensity level is computed by applying a Wiener Filter, as described above, with a filter support of [21×21]. This term is subtracted from the L channel to generate the contrast image. The contrast image has both negative and positive components. The regions with negative contrast values are called low-texture regions, and the regions with high contrast values are called high-texture regions.

At 1303L, for segmenting the low-texture regions (i.e., large pores), a negative threshold (−2.5 typical) is applied to the negative contrast image. The segmented texture lesions are indexed and labeled and the areas of the lesions are also recorded. Furthermore, a small area threshold (typical 50) is applied to remove small pores and a large area threshold (typical 120) is applied to remove large lesions that are due to the spots and wrinkles. The remaining texture lesions, the majority of which are large pores—and their contrast values for each pixel (low-texture contrast image) are computed at 1305L and recorded. At 1307L, the low-texture regions are subjected to shrinking by applying a morphological dilation operation on the low-texture contrast image with a disk structuring element of perimeter 2, for example. The net effect of this operation is the shrinkage of pores as well as the reduced darkening of pores on facial skin, associated with improving skin condition after effective treatment.

Similarly, at 1303H, for segmenting the high-texture regions (very small white spots) a positive threshold (e.g., 2.5) is applied to the positive contrast image by taking all the pixels greater than this threshold. The segmented texture lesions are labeled and the areas of the lesions are also recorded. A small area threshold (e.g., 30 pixels) is applied to remove very small lesions and a large area threshold (e.g., 300 pixels) is applied to remove large lesions that are due to shine. The remaining texture lesions and their contrast values for each pixel (high-texture contrast image) are computed at 1305H and recorded. At 1307H, the high-texture regions are subjected to shrinking by applying a morphological erosion operation on the high-texture contrast image with a disk structuring element of perimeter of 2, for example. The net effect of this operation is the shrinkage of noticeably large white spots as well as reduced intensity of these features in the face image, again associated with improving skin condition after effective treatment.

At 1309L, the reduced low-texture contrast is multiplied by an enhancement factor $e_l$ and added to the L channel at 1211. Similarly, the high-texture contrast image is multiplied by an enhancement factor $e_h$ and added to the L channel at 1311. Exemplary values for the enhancement factors $e_l$ and $e_h$ are 1.0 and 1.0, respectively. At 1313, the texture-aged image is synthesized by an LAB-to-RGB transformation.

Overall Skin Aging and De-Aging Simulation

Figure 14:
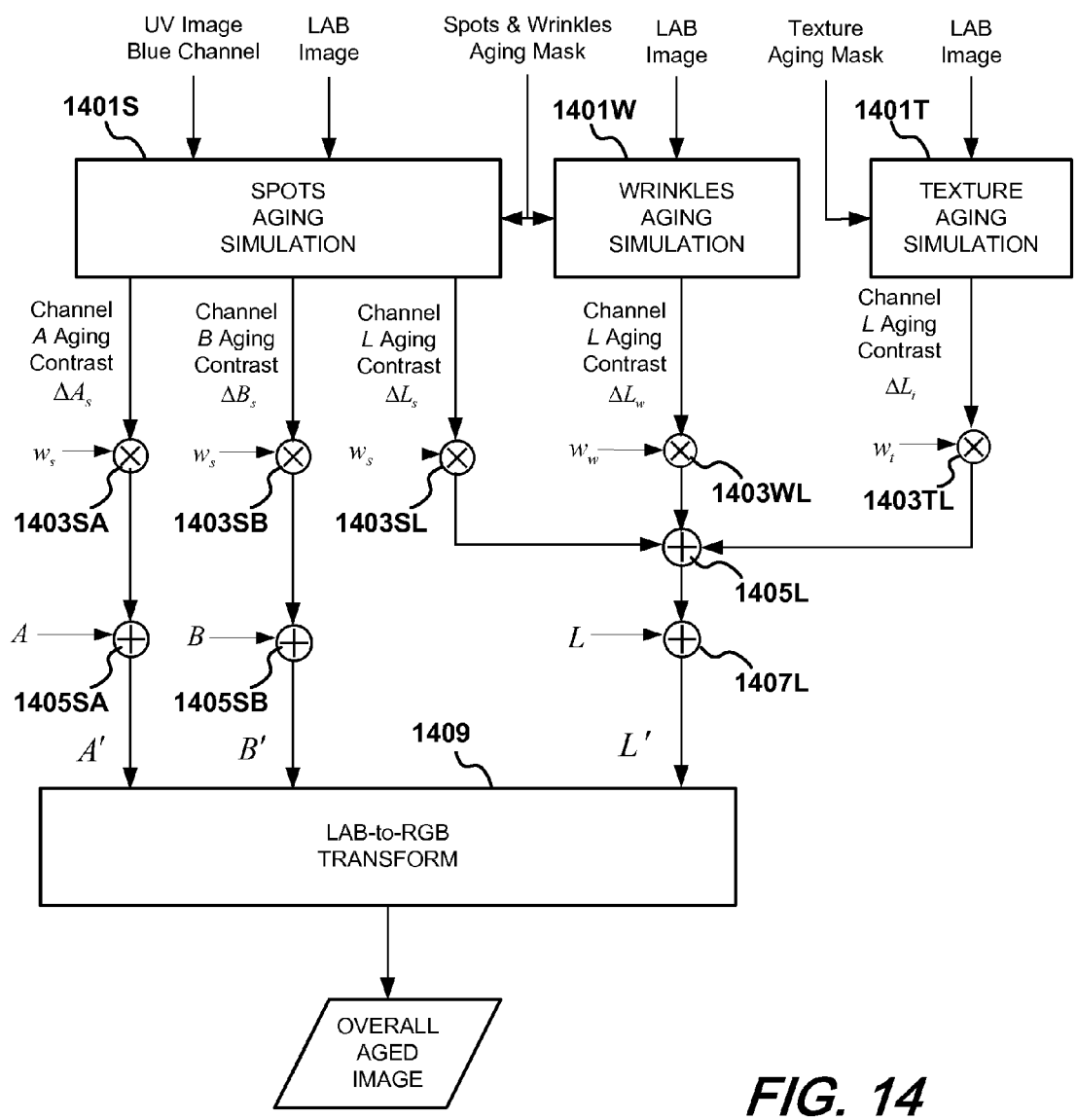
FIG. 14 is a flowchart of an exemplary process for combining the simulation of facial skin aging as indicated by spots, wrinkles and texture, in accordance with the present invention.

The simulation of facial skin aging due to spots, wrinkles and texture described above can be combined to simulate the overall aging of facial skin. FIG. 14 is a flowchart of an exemplary process for doing so. The overall aged image is synthesized in the LAB domain by modifying the L, A and B channels with the aging contrasts for spots, wrinkles and texture. As shown in FIG. 14, in order to incorporate spots, wrinkles and texture aging into the overall process, aging contrast images in the L, A and B channels are generated at 1401S; a wrinkles aging contrast image in the L channel is generated at 1401W; and a texture aging contrast image in the L channel is generated at 1401T. The A, B and L channel spots aging images are each weighted by a factor $w_s$ at 1403SA, 1403SB and 1403SL, respectively; the L channel wrinkle aging image is weighted by a factor $w_w$ at 1403WL; and the L channel texture aging image is weighted by a factor $w_t$ at 1403TL. The three weighting factors $w_s$, $w_w$, and $w_t$ are selected to emphasize or de-emphasize the contribution of the respective component to the overall aged image. The weighted A and B channel spots aging images are added to the A and B channels of the final image at 1405SA and 1405SB, respectively. The weighted L channel spots, wrinkle, and texture images are combined at 1405L and added to the L channel of the final image at 1407L. The L, A and B channels, thus modified, are subjected to an LAB-to-RGB transformation at 1409 to generate the overall aged image in the RGB domain.

Figure 15:
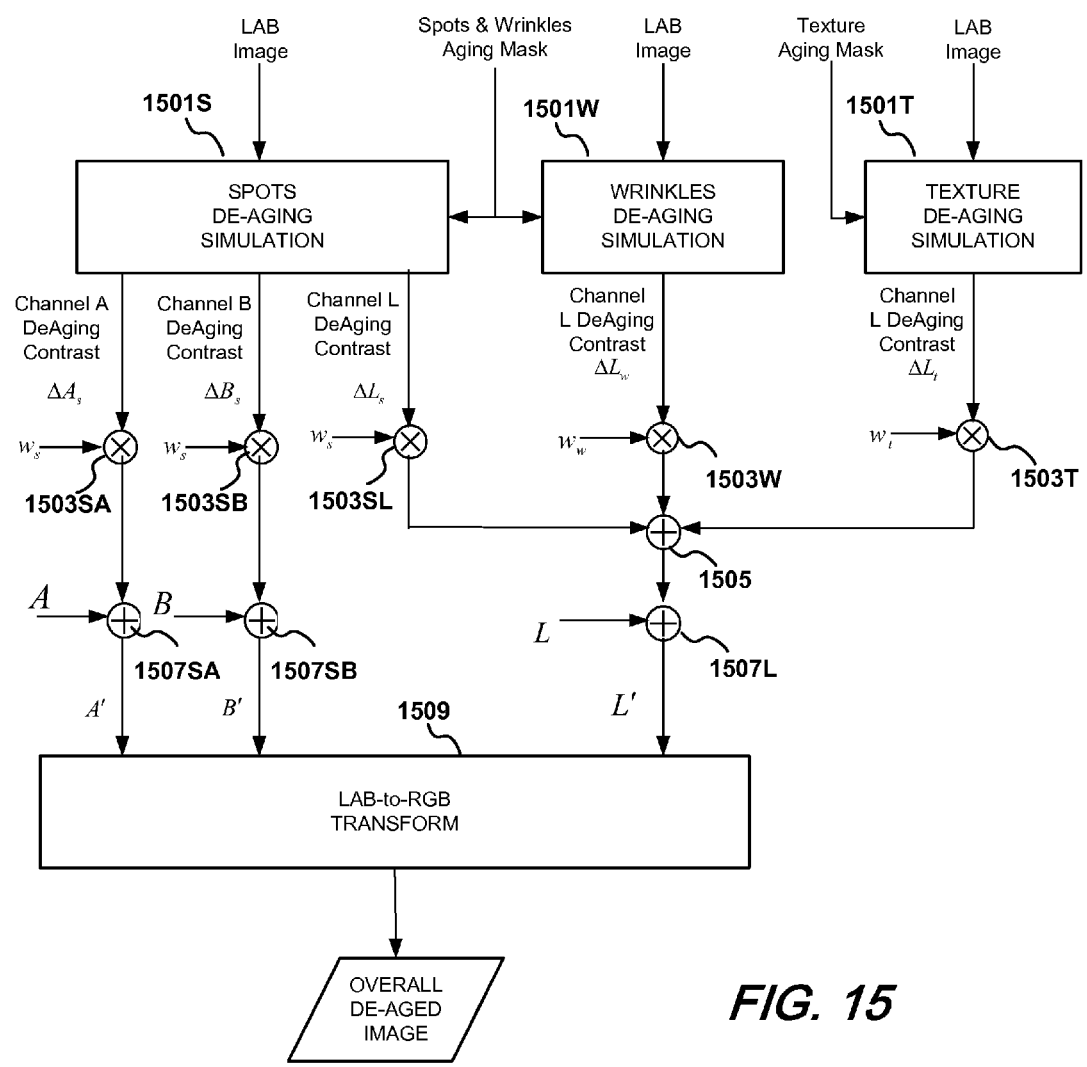
FIG. 15 is a flowchart of an exemplary process for combining the simulation of facial skin de-aging as indicated by spots, wrinkles and texture, in accordance with the present invention.

In a similar manner, the simulation of facial skin de-aging due to spots, wrinkles, and texture described above can be combined to simulate the overall de-aging of facial skin. FIG. 15 is a flowchart of an exemplary process for doing so. De-aging contrasts in channel L, A, and B are generated by respective spots, wrinkles and texture de-aging simulations at 1501SL, 1501SA, 1501SB, and 1501W, and 1501T, respectively. Each contrast image in L is weighted at 1503SL, 1503W and 1503T, by a respective weighting factor, $w_s$, $w_w$, and $w_t$, to emphasize or de-emphasize the contribution of the respective component to the overall de-aged image. The preferred values for these weighting factors are all 1. The weighted L channel spots, wrinkle, and texture contrast images are combined at 1505 and added to the L channel of the final image at 1507. Similarly, the spots contrasts in A is weighted by $w_s$ at 1503SA and added to the A channel at 1507SA. The spots contrasts in B weighted by $w_s$ at 1503SB and added to the B channel at 1507SB to get the final A and B channels. An LAB-to-RGB transformation at 1509 generates the overall de-aged image in the RGB domain. In the final image, prominent skin features (spots, wrinkles) are eliminated and small skin features (pores) are reduced. Such an image can be very useful to predict how the subject skin face might look after a treatment applied for hyperpigmentation, wrinkles or skin texture.

Interactive Tool for Skin Aging/De-Aging Simulation

Skin aging/de-aging simulation in accordance with an exemplary embodiment of the present invention can be demonstrated on a computer monitor by displaying the original image and a simulated image side by side and providing an interactive slider control to allow a viewer to adjust the degree of aging. Depending on the desired simulation (spots, wrinkles, texture or any combination of those), the aged or de-aged image is blended with the original image with the degree of blending depending on the slider position. When the slider is in a neutral position, the original image is displayed in both the left and right panels. When a user moves the slider up, de-aging simulation image is displayed on the right panel, by alpha-blending the original image with the de-aged image. Similarly, when the user moves the slider down, aging simulation image is displayed, by alpha-blending the original image with the aged image. Alpha-blending is a linear weighting of two images and a standard operation commonly used in the art to blend two images. For this application, the various aged and de-aged images for spots, wrinkles, and texture can be generated off-line with the alpha-blending and image rendering preferably performed in real time.

It should be noted that in each of the aging and de-aging simulations described above, the extent of aging or de-aging that is to be simulated is preferably user-selectable within an appropriate time frame, e.g., 5-10 years to demonstrate natural aging, for example, or several months, to demonstrate de-aging due to treatment.

It is understood that the above-described embodiments are illustrative of only a few of the possible specific embodiments which can represent applications of the invention. Numerous and varied other arrangements can be made by those skilled in the art without departing from the spirit and scope of the invention.

Appendix

A-1. Wiener Filter

Given an [M×N] gray image g whose value at the coordinate (i,j) is given by g(i,j), the following steps implement the Wiener Filter using a local [K×K] analysis window centered at (i,j), where K is an odd number.

1. Compute local mean $\mu(i,j)$ and local variance $\sigma^2(i,j)$ in the [K×K] neighborhood of the current pixel located at (i,j) where the pixel value is g(i,j):

$$L = (K-1)/2$$

$$\mu(i,j) = \sum_{m=-L}^{L}\sum_{n=-L}^{L} g(i+m, j+n)$$

$$\sigma^2(i,j) = -\mu(i,j)^2 + \sum_{m=-L}^{L}\sum_{n=-L}^{L} g^2(i+m, j+n)$$

2. Compute noise variance $\sigma_w^2$ by averaging the local variance across the whole image
3. Compute the filtered image pixel value f(i,j) by the following update equations:

If $\sigma^2(i,j) > \sigma_w^2$ $$f(i,j) = \mu(i,j) + \frac{(\sigma^2(i,j) - \sigma_w^2)}{\sigma^2(i,j)}(g(i,j) - \mu(i,j))$$

Else $$f(i,j) = \mu(i,j)$$

4. Repeat Step 3 for all the pixels in the image.

A-2. Ridge Map Generation

Perform the following computational steps for each pixel coordinate (i,j) in the region-of-interest (ROI):

1. Obtain the following quantities from the ridge detector:
   R(i,j): Ridge strength, a real positive number
   V(i,j): Ridge orientation vector, a 2-element vector with real numbers.
2. Based on these quantities, compute the directional strength as the sum of inner products of the orientation vectors in the 8-connected neighborhood:

$$Ds(i,j) = \sum_{n=1}^{8} \langle V_c, V_n \rangle,$$

where $\langle . \rangle$ denotes inner product operation, and $V_c$ denotes the ridge orientation vector of the current pixel, and $V_c$ denotes the ridge orientation vector of the n-th pixel in the neighborhood.
3. Add a portion of directional strength to the ridge strength to compute ridge map:
   $Rm(i,j)=R(i,j)+\alpha Ds(i,j)$ where $\alpha$ is a weighting factor in the range [0.2 0.5]

| A-3. DEFINITIONS OF SHAPE PROPERTIES | |
|---|---|
| Property | Definition |
| Area | Number of pixels in the Object |
| Major-Axis-Length | The length (in pixels) of the major axis of the ellipse that has the same normalized second central moments as the Object. |
| Minor-Axis-Length | The length (in pixels) of the minor axis of the ellipse that has the same normalized second central moments as the Object. |
| Extent | The proportion of the pixels in the bounding box that are also in the object. Bounding box is the smallest rectangle that contains the Object. |
| Eccentricity | The eccentricity of the ellipse that has the same second-moments as the Object. The eccentricity is the ratio of the distance between the foci of the ellipse and its major axis length. |
| Solidity | The proportion of the pixels in the convex hull that are also in the Object. Convex hull is the smallest convex polygon that contains the Object. |

What is claimed is:

1. A method of manipulating a facial image so as to simulate time-related changes, the method comprising:
   transforming the facial image to a color space format having intensity and color components, segmenting out the face region using a thresholding procedure wherein the thresholding procedure includes Otsu thresholding:
   manipulating the facial image to generate a spot change intensity component;
   manipulating the facial image to generate a wrinkle change intensity component;
   manipulating the facial image to generate a texture change intensity component; and
   modifying the intensity component of the facial image based on a combination of the spot change intensity component, wrinkle change intensity component, and texture change intensity component, thereby generating a spot, wrinkle and texture changed facial image;
   wherein there is further generated a first spot, wrinkle and texture changed facial image which is an aged facial image, and a second spot, wrinkle and texture changed facial image which is a de-aged facial image, wherein the aged or de-aged facial image is selectively blended with the facial image to generate a composite image, and displaying the composite image.

2. The method of claim 1, wherein the spot, wrinkle and texture changed facial image is a de-aged facial image.

3. The method of claim 1, comprising:
   manipulating the facial image to generate a first spot change color component, and a second spot change color component;
   modifying a first color component of the facial image based on the first spot change color component; and
   modifying a second color component of the facial image based on the second spot change color component,
   wherein the spot, wrinkle and texture changed facial image is an aged facial image.

4. The method of claim 1, comprising:
   applying a mask to the facial image before manipulating the facial image.

5. The method of claim 4, wherein the mask includes a first mask for spot and wrinkle simulation and a second mask for texture simulation.

6. The method of claim 1, wherein the color space format having intensity and color components is an LAB format having a luminosity component L and color components A and B.

* * * * *